US012048477B2

(12) United States Patent
Stamm et al.

(10) Patent No.: US 12,048,477 B2
(45) Date of Patent: Jul. 30, 2024

(54) METHOD OF REPROCESSING A SURGICAL INSTRUMENT

(71) Applicant: Covidien LP, Mansfield, MA (US)

(72) Inventors: Stephen J. Stamm, Wheat Ridge, CO (US); Purvishkumar H. Soni, Longmont, CO (US); Alyssa M. Sawyer, Broomfield, CO (US); Subhadeep Saha, Boulder, CO (US); Jessica E. C. Olson, Frederick, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/137,044

(22) Filed: Apr. 20, 2023

(65) Prior Publication Data
US 2023/0248420 A1    Aug. 10, 2023

Related U.S. Application Data

(62) Division of application No. 17/480,441, filed on Sep. 21, 2021, now Pat. No. 11,642,164, which is a
(Continued)

(51) Int. Cl.
*A61B 18/14*    (2006.01)
*B23P 6/00*    (2006.01)
(Continued)

(52) U.S. Cl.
CPC ............ *A61B 18/1445* (2013.01); *B23P 6/00* (2013.01); *B23P 19/04* (2013.01); *A61B 2017/00017* (2013.01); *A61B 2017/00367* (2013.01); *A61B 2017/00473* (2013.01); *A61B 34/30* (2016.02); *Y10T 29/49815* (2015.01)

(58) Field of Classification Search
CPC ...... A61B 18/1445; A61B 2017/00473; A61B 34/30; A61B 2017/00017; A61B 2017/00367; A61B 2018/00589; A61B 2018/0063; A61B 2018/00601;
(Continued)

(56) References Cited

U.S. PATENT DOCUMENTS

| 5,342,391 A | 8/1994 | Foshee et al. |
| 5,605,272 A | 2/1997 | Witt et al. |

(Continued)

FOREIGN PATENT DOCUMENTS

| AU | 2004216575 A1 | 4/2005 |
| AU | 2006225179 A1 | 4/2007 |

(Continued)

*Primary Examiner* — Sarang Afzali
(74) *Attorney, Agent, or Firm* — Carter, DeLuca & Farrell LLP

(57) ABSTRACT

A method of disassembling a surgical instrument for reprocessing, includes accessing an interior housing of a surgical instrument to expose a slider assembly, an elongated outer shaft including a drive plate and knife assembly extending therethrough, and a torsion spring of the surgical instrument. The method further includes grasping an upper leg of the torsion spring to disengage the upper leg from a slot defined within the drive plate, disengaging the drive plate from the slider assembly, and removing the torsion spring from the slider assembly.

15 Claims, 22 Drawing Sheets

Related U.S. Application Data division of application No. 15/960,964, filed on Apr. 24, 2018, now Pat. No. 11,123,133.

(51) Int. Cl.
  *B23P 19/04* (2006.01)
  *A61B 17/00* (2006.01)
  *A61B 34/30* (2016.01)

(58) Field of Classification Search
  CPC ....... A61B 2090/034; A61B 2018/1455; B23P 19/04; B23P 19/048; Y10T 29/49815
  See application file for complete search history.

(56) References Cited

U.S. PATENT DOCUMENTS

| | | | |
|---|---|---|---|
| 5,891,142 A | 4/1999 | Eggers et al. | |
| 5,919,206 A | 7/1999 | Gengler et al. | |
| 5,935,126 A | 8/1999 | Riza | |
| 6,056,866 A * | 5/2000 | Maeda | C02F 1/4618 204/263 |
| 6,077,287 A | 6/2000 | Taylor et al. | |
| 6,129,740 A | 10/2000 | Michelson | |
| 6,322,579 B1 | 11/2001 | Muller | |
| 6,334,860 B1 | 1/2002 | Dorn | |
| 6,443,968 B1 | 9/2002 | Holthaus et al. | |
| 6,506,208 B2 | 1/2003 | Hunt et al. | |
| 6,706,056 B2 | 3/2004 | Bacher | |
| 6,770,072 B1 | 8/2004 | Truckai et al. | |
| 6,790,217 B2 | 9/2004 | Schulze et al. | |
| 6,887,240 B1 | 5/2005 | Lands et al. | |
| 7,052,496 B2 | 5/2006 | Yamauchi | |
| 7,147,638 B2 | 12/2006 | Chapman et al. | |
| 7,150,097 B2 | 12/2006 | Sremcich et al. | |
| 7,384,420 B2 | 6/2008 | Dycus et al. | |
| 7,494,501 B2 | 2/2009 | Ahlberg et al. | |
| 7,549,988 B2 | 6/2009 | Eberl et al. | |
| 7,559,940 B2 | 7/2009 | McGuire et al. | |
| 7,753,909 B2 | 7/2010 | Chapman et al. | |
| 7,758,608 B2 | 7/2010 | DiCesare et al. | |
| 7,766,910 B2 | 8/2010 | Hixson et al. | |
| 7,877,853 B2 | 2/2011 | Unger et al. | |
| 7,922,953 B2 | 4/2011 | Guerra | |
| 8,241,320 B2 | 8/2012 | Yons et al. | |
| 8,252,021 B2 | 8/2012 | Boulnois et al. | |
| 8,266,783 B2 | 9/2012 | Brandt et al. | |
| 8,376,957 B2 | 2/2013 | Hibner | |
| 8,388,646 B2 | 3/2013 | Chojin | |
| 8,394,094 B2 | 3/2013 | Edwards et al. | |
| 8,409,244 B2 | 4/2013 | Hinman et al. | |
| 8,545,534 B2 | 10/2013 | Ahlberg et al. | |
| 8,551,090 B2 | 10/2013 | Sutter et al. | |
| 8,728,118 B2 | 5/2014 | Hinman et al. | |
| 8,740,933 B2 | 6/2014 | Anderson | |
| 8,789,741 B2 | 7/2014 | Baxter, III et al. | |
| 8,814,856 B2 | 8/2014 | Elmouelhi et al. | |
| 8,858,553 B2 | 10/2014 | Chojin | |
| 11,123,133 B2 | 9/2021 | Stamm et al. | |
| 11,642,164 B2 | 5/2023 | Stamm et al. | |
| 2005/0090837 A1 | 4/2005 | Sixto et al. | |
| 2010/0063525 A1 | 3/2010 | Beaupre et al. | |
| 2010/0198220 A1 | 8/2010 | Boudreaux et al. | |
| 2011/0073246 A1 | 3/2011 | Brandt et al. | |
| 2011/0270251 A1 | 11/2011 | Horner et al. | |
| 2013/0304058 A1 | 11/2013 | Kendrick | |
| 2014/0025073 A1 | 1/2014 | Twomey et al. | |
| 2016/0338764 A1 | 11/2016 | Krastins et al. | |
| 2017/0049916 A1 * | 2/2017 | Ikeda | B65B 5/045 |

FOREIGN PATENT DOCUMENTS

| | | |
|---|---|---|
| CA | 2844067 A1 | 9/2014 |
| EP | 2319447 A1 | 5/2011 |
| EP | 2628459 A2 | 8/2013 |
| EP | 3064163 A1 | 9/2016 |
| EP | 3095399 A2 | 11/2016 |

* cited by examiner

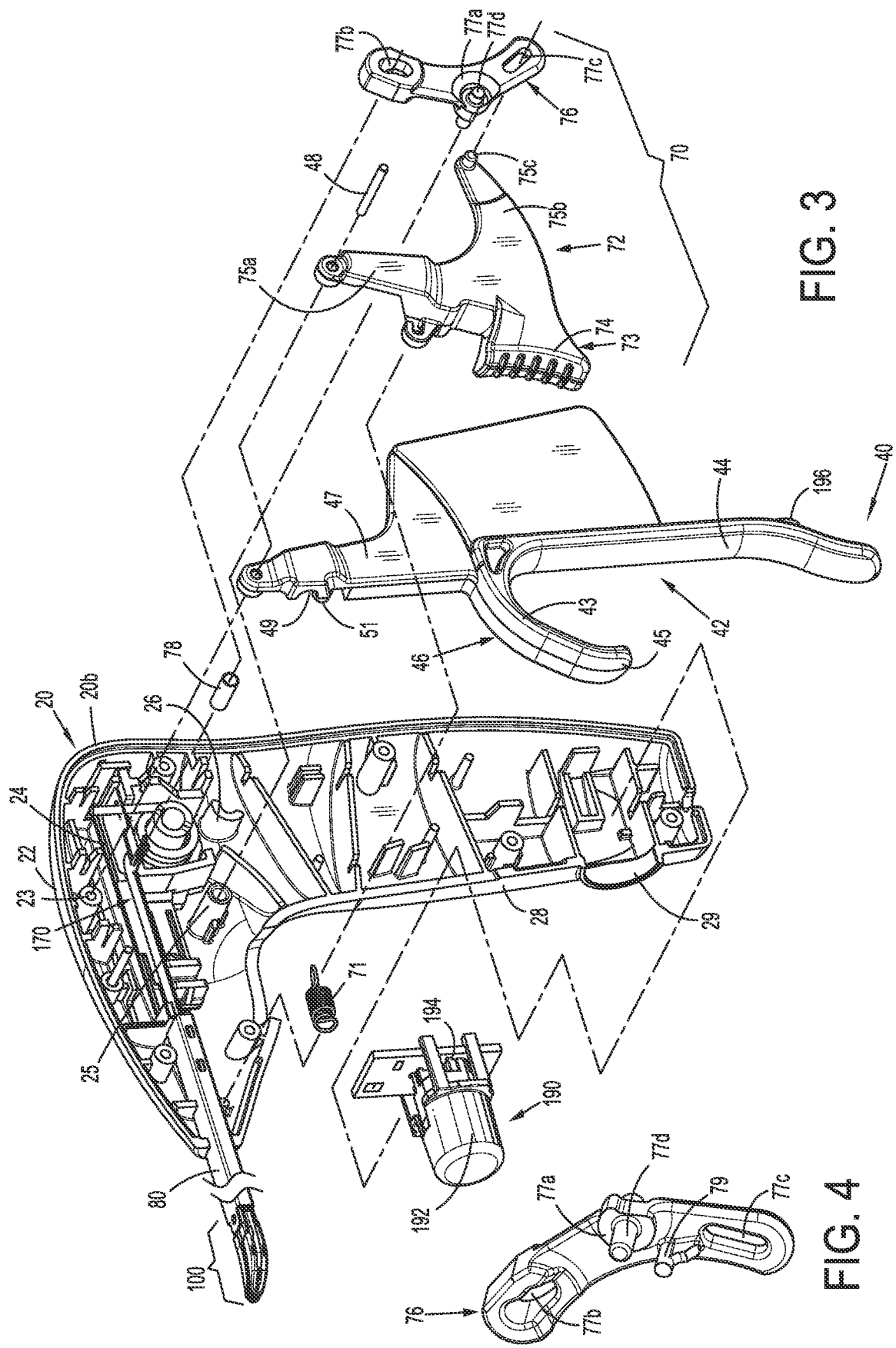

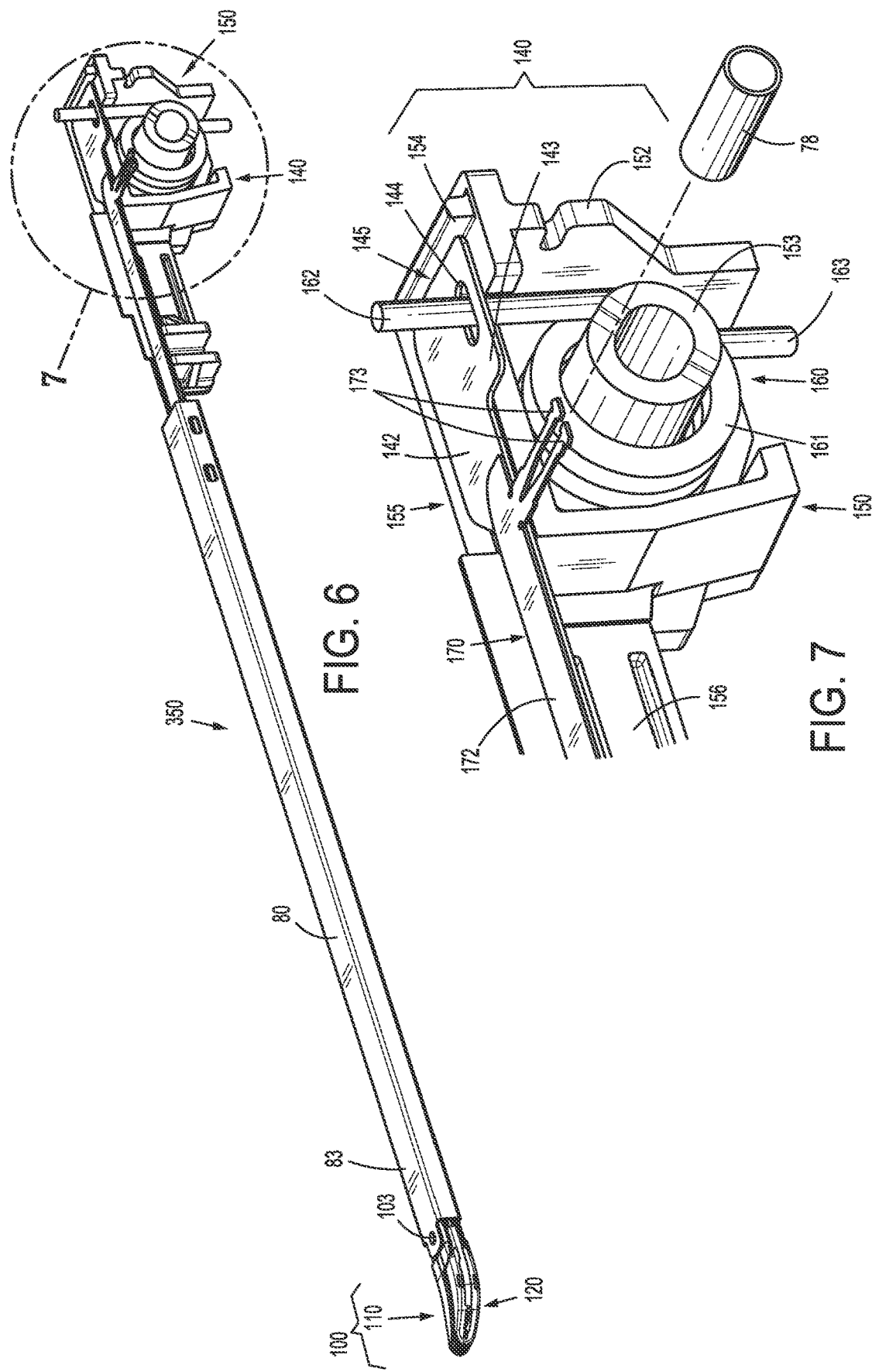

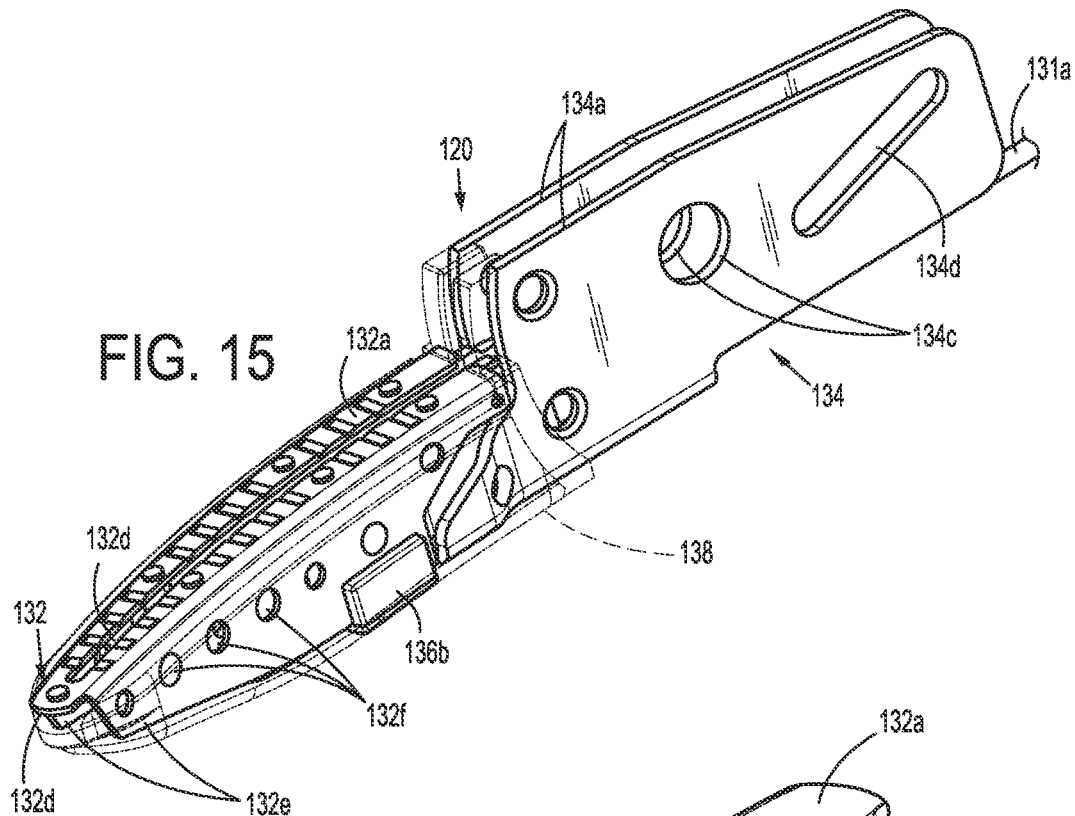
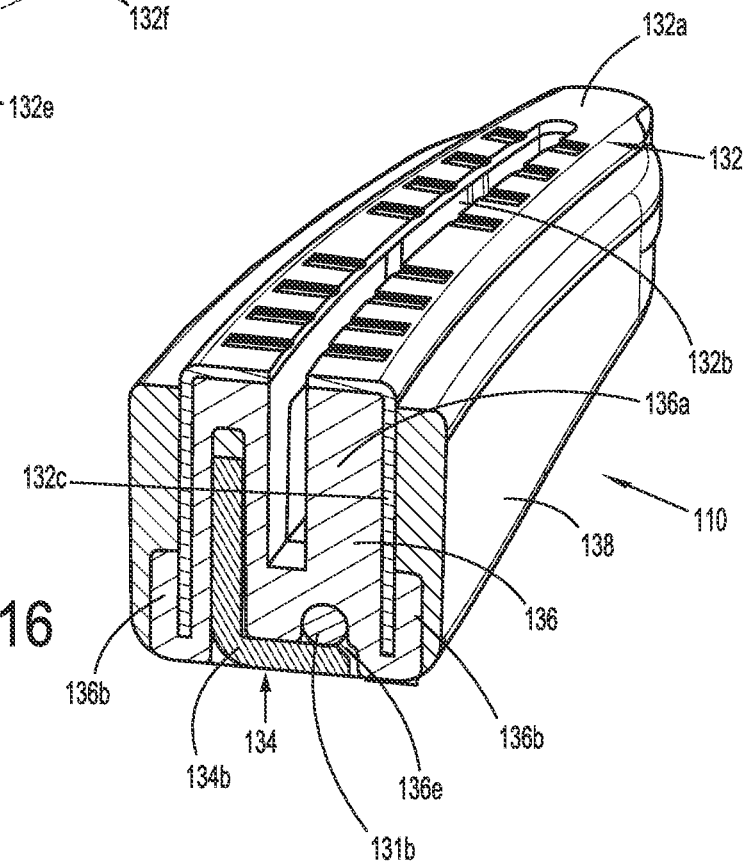

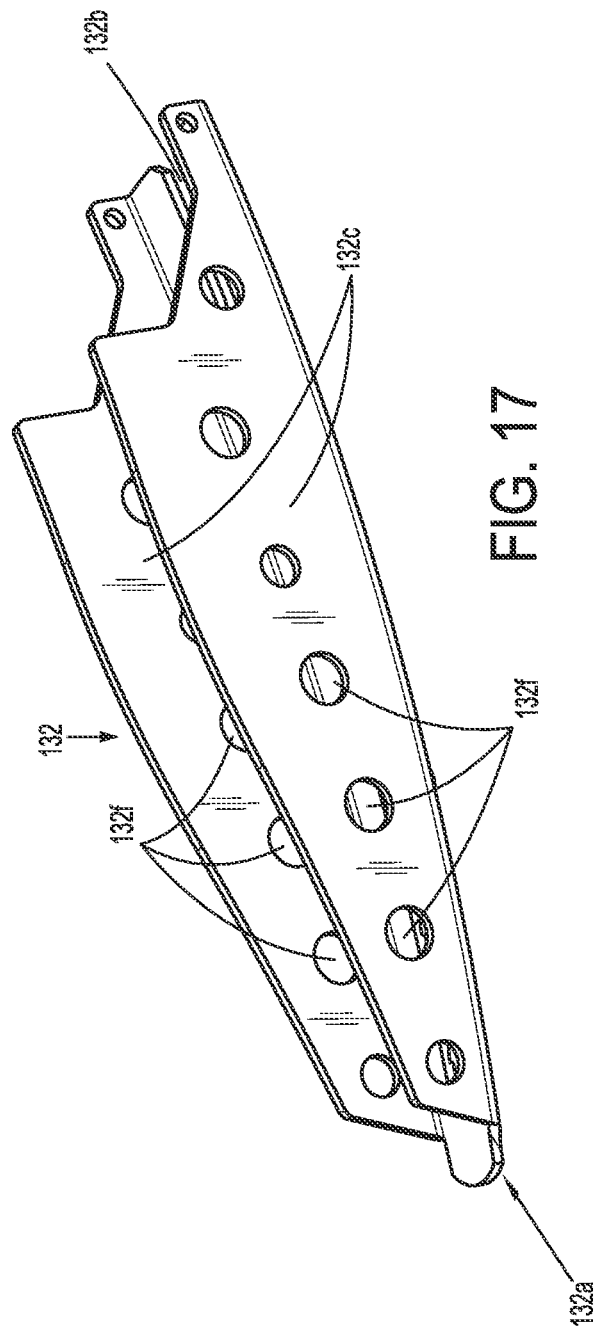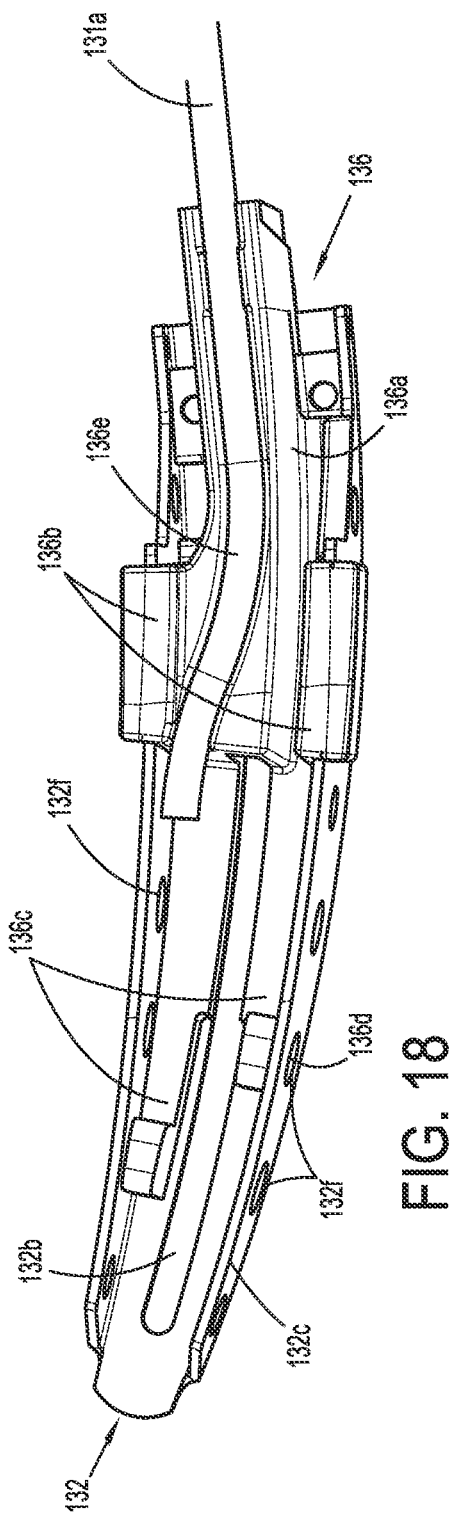

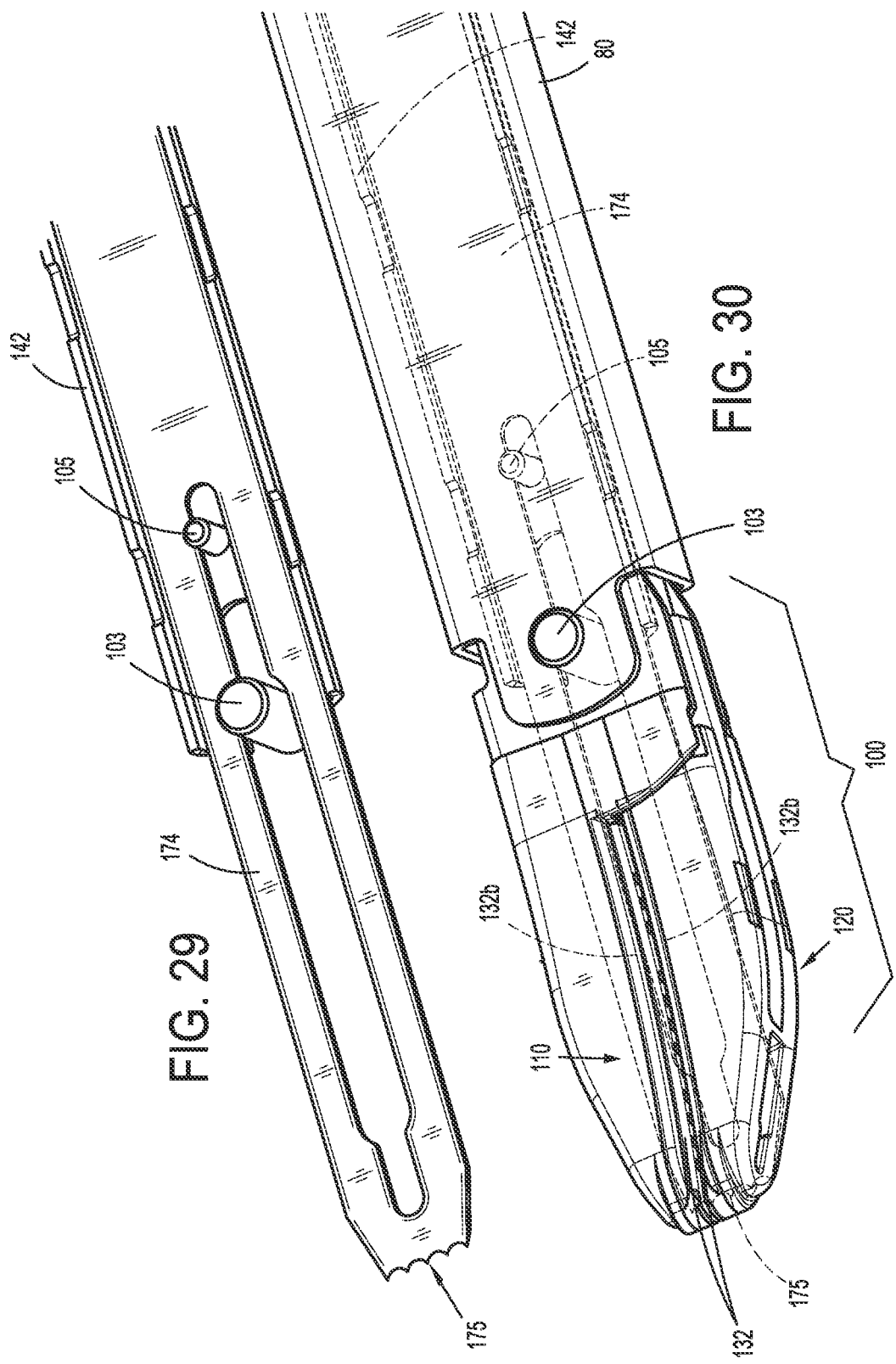

METHOD OF REPROCESSING A SURGICAL INSTRUMENT

CROSS-REFERENCE TO RELATED APPLICATIONS

This application is a divisional of U.S. patent application Ser. No. 17/480,441, filed on Sep. 21, 2021, now U.S. Pat. No. 11,642,164, which is a divisional of U.S. patent application Ser. No. 15/960,964, filed on Apr. 24, 2018, now U.S. Pat. No. 11,123,133.

FIELD

The present disclosure relates to methods of reprocessing surgical instruments, and, more particularly, methods of reprocessing surgical instruments for use with tonsillectomies, adenoidectomies, and other surgical procedures.

BACKGROUND

The tonsils and adenoids are part of the lymphatic system and are generally located in the back of the throat. These parts of the lymphatic system are generally used for sampling bacteria and viruses entering the body and activating the immune system when warranted to produce antibodies to fight oncoming infections. More particularly, the tonsils and adenoids break down the bacteria or virus and send pieces of the bacteria or virus to the immune system to produce antibodies for fighting off infections.

Inflammation of the tonsils and adenoids (e.g., tonsillitis) impedes the ability of the tonsils and adenoids to destroy the bacteria resulting in a bacterial infection. In many instances, the bacteria remain even after treatment and serve as a reservoir for repeated infections (e.g., tonsillitis or ear infections).

A tonsillectomy and/or adenoidectomy may be performed when infections persist and antibiotic treatments fail. Some individuals are also born with larger tonsils that are more prone to cause obstruction. An adenoidectomy may also be required to remove adenoid tissue when ear pain persists, or when nose breathing or function of the Eustachian tube is impaired. Often times, tonsillectomy and adenoidectomy procedures are performed at the same time.

Instruments used in the various procedures are often categorized into reusable instruments (i.e., instruments that may be used again after sterilization), disposable instruments (i.e., instruments where it is intended that the entire instrument be discarded after use in an environmentally safe fashion), and reposable instruments (i.e., where in at least one part of a disposable instrument is reusable after sterilization). A new class of so called reprocessed instruments has recently been introduced by manufacturers for use with various surgical procedures. Typically, these instruments are disposable instruments (or possibly reposable instruments) that are collected after a surgical use, disassembled, sterilized, re-assembled and sold as reprocessed instruments. In many cases, most of the original parts are cannibalized to provide the necessary parts for reassembly of the same surgical instrument. Parts that wear during use, are broken during disassembly, and/or are otherwise unable to be reprocessed may be replaced with new components.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A method of disassembling a surgical instrument for reprocessing includes accessing an interior housing of a surgical instrument to expose a slider assembly, an elongated outer shaft including a drive plate and knife assembly extending therethrough, and a torsion spring of the surgical instrument. The method further includes grasping an upper leg of the torsion spring to disengage the upper leg from a slot defined within the drive plate, disengaging the drive plate from the slider assembly, and removing the torsion spring from the slider assembly. In aspects, the torsion spring is disengaged from the slot defined in the drive plate by rotating the torsion spring in a first direction.

In aspects, the method may further include removing a pivot pin from an end effector assembly of the surgical instrument, exposing a cam pin of the end effector assembly, removing the cam pin from the end effector assembly, and releasing the end effector assembly from the drive plate. In other aspects the method may include retaining the elongated outer shaft in place while removing the drive plate and a knife blade of the knife assembly from the elongated outer shaft. Still other aspects may include disengaging the knife blade from the drive plate, removing a pair of jaw wires from a wire guide disposed in the housing by unrouting the wires therefrom, and/or removing the end effector assembly and the jaw wires from a distal end of the elongated outer shaft.

In yet other aspects the method may include sterilizing at least one of the slider assembly, elongated outer shaft, end effector assembly, wire guide, jaw wires, knife assembly, knife blade, torsion spring, or drive plate.

According to another aspect, the present disclosure includes a method of disassembling a surgical instrument for reprocessing including separating a first housing half from a second housing half to expose a front end assembly, a trigger assembly, and a movable handle of a surgical instrument. The method may further include disengaging a biasing spring from the second housing half to enable removal of the trigger assembly from the surgical instrument, removing a pivot pin to enable removal of the movable handle from the second housing half, removing the front end assembly from the second housing half, and sterilizing the front end assembly. The front end assembly may be sterilized by autoclaving the front end assembly, introducing the front end assembly into a sterilization bath and/or applying a pressurized fluid to the front end assembly. In aspects, the front end assembly includes an elongated shaft, end effector assembly, drive plate, and/or knife plate.

According to another aspect, the present disclosure includes a method of disassembling a surgical instrument for reprocessing including separating a first housing half from a second housing half to expose a front end assembly, a trigger assembly, and a movable handle of a surgical instrument. In aspects, the front end assembly includes an elongated shaft, end effector assembly, drive plate, and/or knife plate. The method also includes disengaging a biasing spring from the second housing half to enable removal of the trigger assembly from the surgical instrument, removing a pivot pin to enable removal of the movable handle from the second housing half, removing the front end assembly from the second housing half, orienting the front end assembly to expose a slider assembly, an elongated outer shaft including a drive plate and knife assembly extending therethrough, and a torsion spring, grasping an upper leg of the torsion spring to disengage the upper leg from a slot defined within the drive plate, disengaging the drive plate from the slider assembly, and removing the torsion spring from the slider assembly.

In aspects, the torsion spring is disengaged from the slot defined in the drive plate by rotating the torsion spring in a first direction. In other aspects, the method may further include removing a pivot pin from an end effector assembly of the surgical instrument, exposing a cam pin of the end effector assembly, removing the cam pin from the end effector assembly, and releasing the end effector assembly from the drive plate. In other aspects the method may include retaining the elongated outer shaft in place while removing the drive plate and a knife blade of the knife assembly from the elongated outer shaft. Still other aspects may include disengaging the knife blade from the drive plate, removing a pair of jaw wires from a wire guide disposed in the housing by unrouting the wires therefrom, and/or removing the end effector assembly and the jaw wires from a distal end of the elongated outer shaft.

In still other aspects, the method may include sterilizing the slider assembly, elongated outer shaft, end effector assembly, wire guide, jaw wires, knife assembly, knife blade, torsion spring, and/or drive plate.

BRIEF DESCRIPTION OF THE DRAWINGS

Various aspects and features of the present disclosure described herein with reference to the drawings wherein:

FIG. 3 is a front, perspective, partially-exploded view of the surgical instrument of FIG. 1 with the jaw members disposed in the approximated position and a portion of the housing removed to illustrate the internal components thereof;

FIG. 4 is an enlarged, perspective view of the linkage of the trigger assembly of the surgical instrument of FIG. 1;

FIG. 6 is a front, perspective view of the drive assembly, shaft, and end effector assembly of the surgical instrument of FIG. 1;

FIG. 7 is an enlarged, perspective view of the area of detail indicated as "7" in FIG. 6;

FIG. 12' is an enlarged, perspective view of the distal end of another knife blade configured for use with the surgical instrument of FIG. 1 or any other suitable surgical instrument;

FIG. 15 is a side, perspective view of one of the jaw members of the surgical instrument of FIG. 1 with a portion thereof removed;

FIG. 16 is a transverse, cross-sectional view of the jaw member of FIG. 15;

FIG. 17 is a perspective view of the electrically-conductive plate of one of the jaw members of the surgical instrument of FIG. 1;

FIG. 18 is a top view of the electrically-conductive plate of one of the jaw members of the surgical instrument of FIG. 1 including an overmolded spacer disposed thereon;

FIG. 29 is a perspective view of the distal end of the drive and knife assemblies of the surgical instrument of FIG. 1 with the knife assembly disposed in an extended position;

FIG. 30 is a perspective view of the distal end of the drive and knife assemblies as shown in FIG. 29 and further including the jaw members disposed in the approximated position;

DETAILED DESCRIPTION

Figure 1:
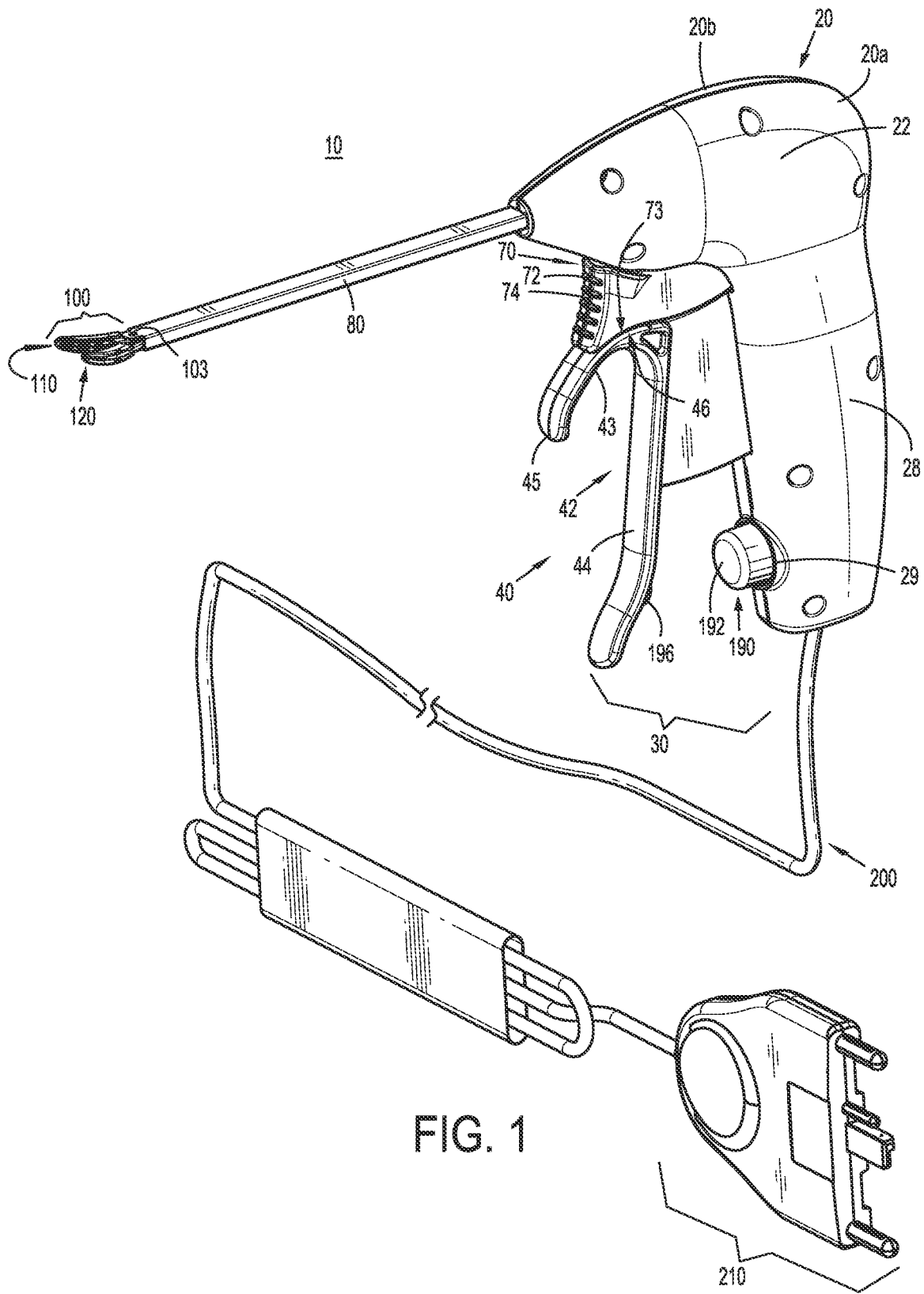
FIG. 1 is a perspective view of a surgical instrument provided in accordance with the present disclosure with jaw members of the end effector assembly of the surgical instrument disposed in a spaced-apart position.

Referring generally to FIG. 1, a surgical instrument provided in accordance with the present disclosure is shown generally identified by reference numeral 10. Instrument 10, as described below, is configured for grasping, treating, and/or dissecting tissue and may find particular applicability for use in performing tonsillectomy procedures and/or adenoidectomy procedures, although use of instrument 10 in various other surgical procedures is also contemplated and within the scope of the present disclosure. Additional features contemplated for use with instrument 10 are detailed in commonly-owned U.S. patent application Ser. No. 14/719,422 (published as US 2016/0338762), Ser. No. 14/719,434 (published as US 2016/0338763), Ser. No. 14/719,452 (published as US 2016/0338718), Ser. No. 14/719,464 (published as US 2016/0338719), and Ser. No. 14/719,475 (published as US 2016/0338764), each of which was filed on May 22, 2015, and is incorporated herein by reference in its entirety.

With reference to FIGS. 1-3, 5, and 10, instrument 10 generally includes a housing 20, a handle assembly 30, a trigger assembly 70, a shaft 80, an end effector assembly 100, a drive assembly 140, a knife assembly 170, and an energy activation assembly 190. As detailed below, shaft 80 extends distally from housing 20 and supports end effector assembly 100 at distal end of shaft 80, drive assembly 140 operably couples handle assembly 30 with end effector assembly 100 to enable selective manipulation of jaw members 110, 120 of end effector assembly 100, knife assembly 170 is operably coupled with trigger assembly 70 to enable selective translation of a knife blade 174 (FIGS. 11 and 12) of knife assembly 170 relative to end effector assembly 100, and energy activation assembly 190 enables energy to be selectively delivered to end effector assembly 100.

Instrument 10 also includes an electrosurgical cable 200 including a proximal plug 210 that connects instrument 10 to a generator (not shown) or other suitable power source, although instrument 10 may alternatively be configured as a battery-powered instrument. Electrosurgical cable 200 includes lead wires, e.g., lead wires 131a, 131b (FIGS. 18 and 31A), extending therethrough that have sufficient length to extend through housing 20 and shaft 80 in order to operably couple the generator, energy activation assembly 190, and end effector assembly 100 with one another to enable the selective supply of energy to electrically-conductive plates 112, 122 of jaw members 110, 120 of end effector assembly 100, e.g., upon activation of activation switch 194 of energy activation assembly 190.

Figure 2:
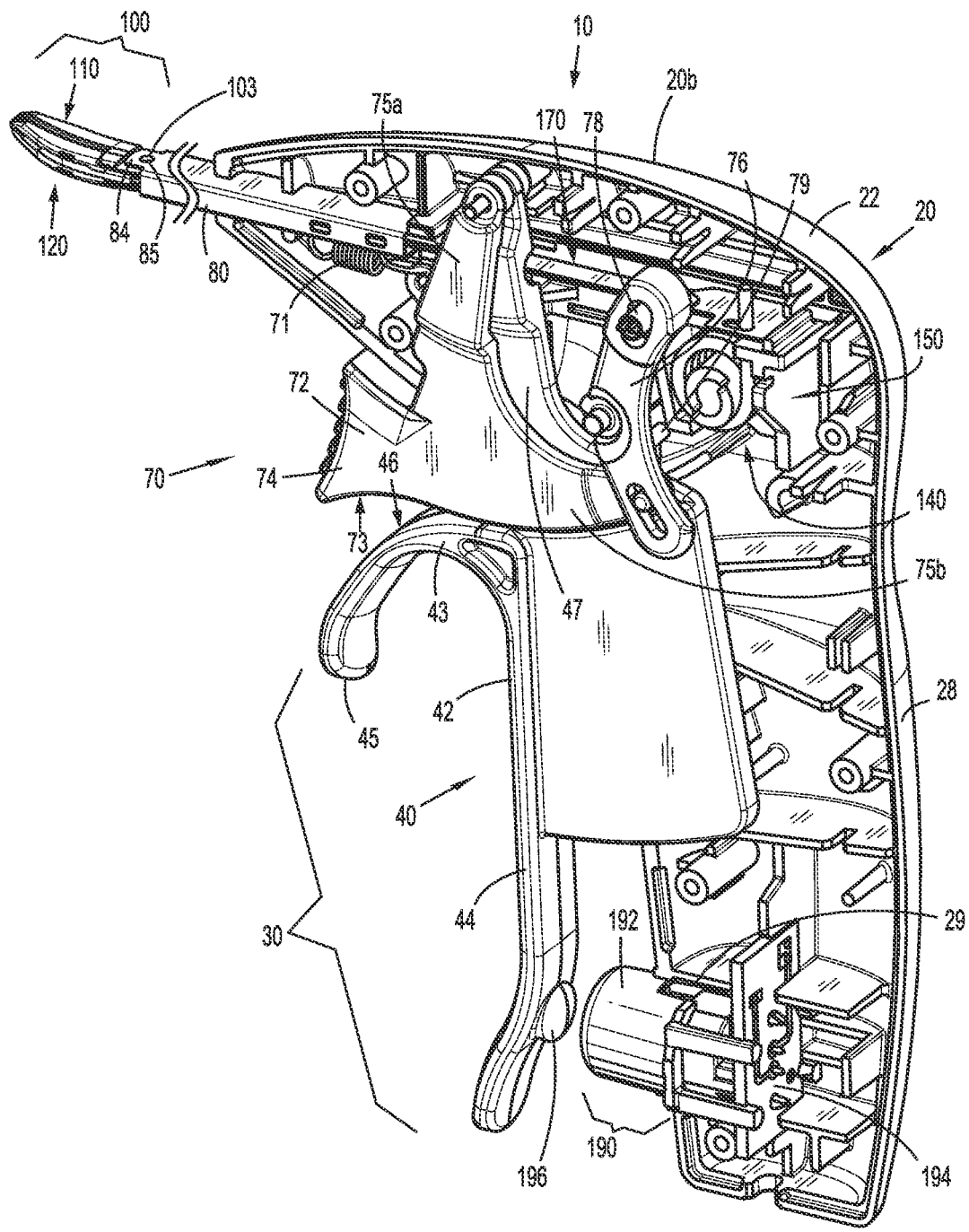
FIG. 2 is a rear, perspective view of the surgical instrument of FIG. 1 with the jaw members disposed in the approximated position and a portion of the housing removed to illustrate the internal components thereof.
Figure 5:
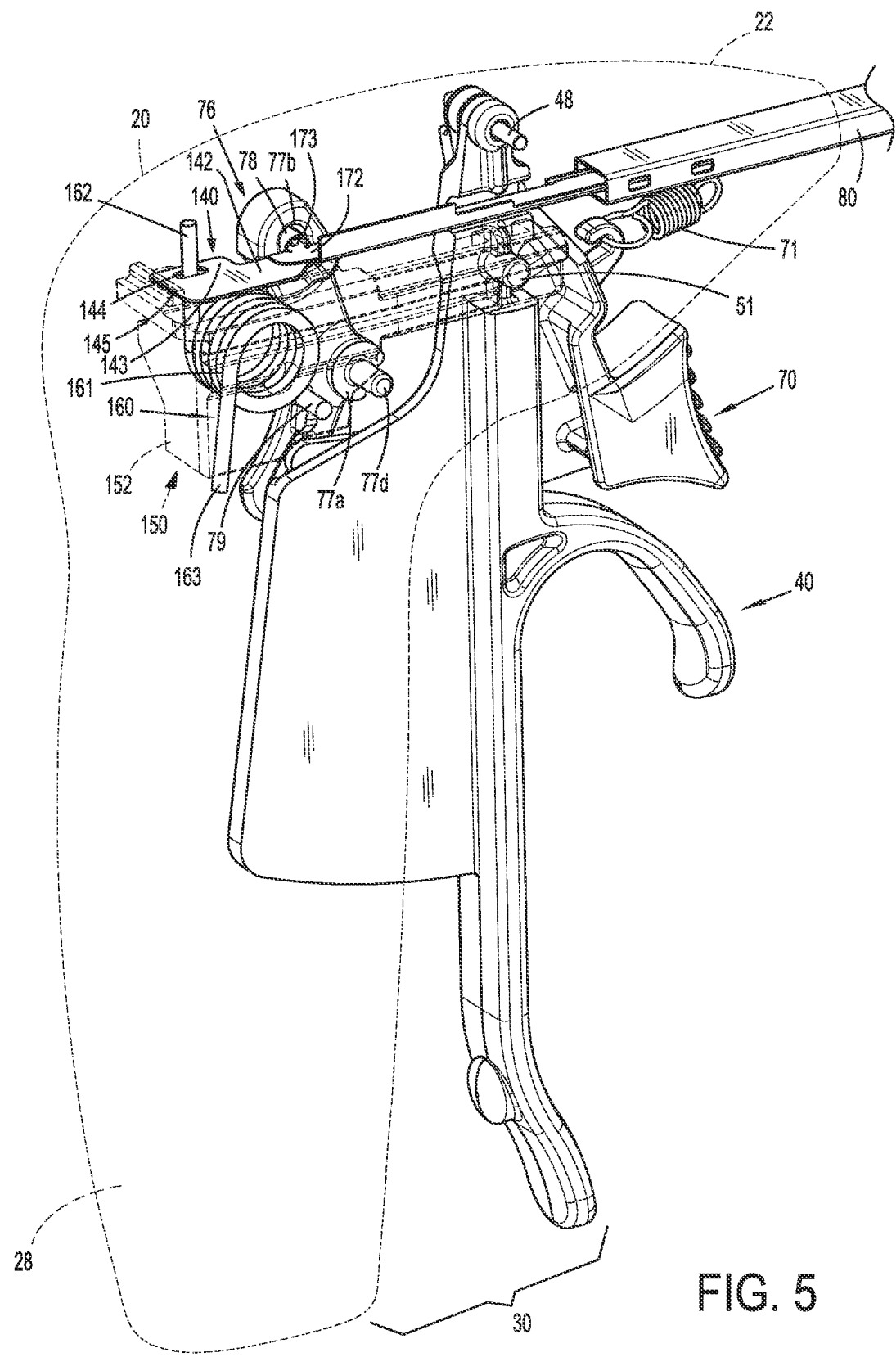
FIG. 5 is a rear, perspective view of the handle, trigger, and drive assemblies of the surgical instrument of FIG. 1 with a movable handle of the handle assembly disposed in a partially-actuated position and a trigger of the trigger assembly disposed in an un-actuated position.
Figure 8:
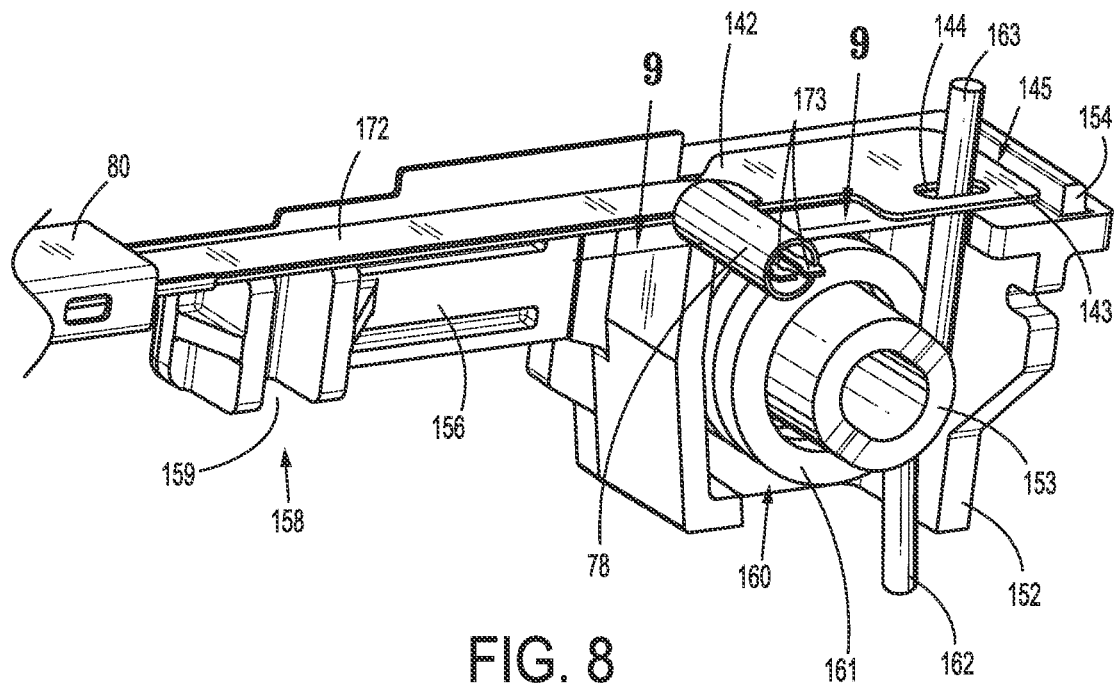
FIG. 8 is another enlarged, perspective view of the proximal end of the drive assembly of the surgical instrument of FIG. 1.
Figure 9:
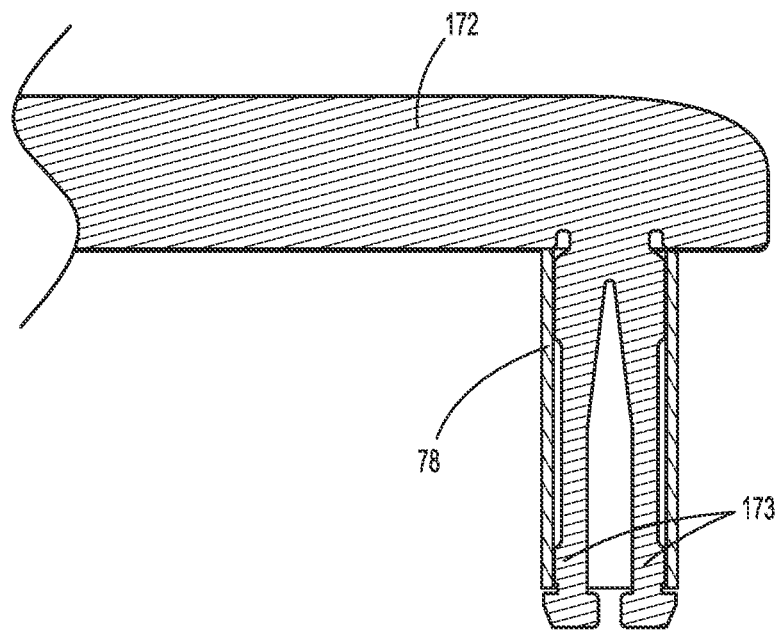
FIG. 9 is a longitudinal, cross-sectional view taken along section line "9-9" of FIG. 8.

Referring to FIGS. 1-3, housing 20 houses the internal working components of instrument 10 and is formed from first and second housing components configured to engage one another via a plurality of pin-aperture engagements spaced around housing 20, although other suitable engagements, e.g., screws, snap-fit connections, adhesion, ultrasonic welding, etc., are also contemplated, as are different formations of housing 20. Housing 20 defines a pistol-style configuration having a longitudinally-extending barrel portion 22 and a fixed handle portion 28 that extends from barrel portion 22 in generally perpendicular orientation relative thereto.

Barrel portion 22 of housing 20 defines a distal aperture configured to receive and engage the proximal end of shaft 80 therein. Shaft 80 extends distally from barrel portion 22 of housing 20 and defines a generally rectangular cross-sectional configuration oriented such that the larger width dimension thereof extends laterally and the smaller height dimension thereof extends vertically. This configuration of shaft 80 relative to the orientation of jaw members 110, 120 provides enhanced "line-of-sight" for visualizing the surgical site adjacent end effector assembly 100. As described in greater detail below, shaft 80 includes a pair of spaced-apart clevis members 84 extending from the top and bottom walls, e.g., the larger width dimension walls, of shaft 80 at a distal end 83 of shaft 80. Each clevis member 84 defines an aperture 86 for receiving a pivot pin 103 to operably support end effector assembly 100 at the distal end of shaft 80.

Barrel portion 22 of housing further includes a pair of opposed pivot apertures 23 (only one of which is shown), a longitudinal track 24, a pair of opposed pivot bosses 25 (only one of which is shown), and a block 26. Each pivot aperture 23 is configured to receive an end of pivot pin 48 to pivotably couple movable handle 40 and trigger 72 to housing 20. Alternatively, a separate pivot pin 48' received between separate pivot apertures 23' (only one of which is shown) may be provided from coupling movable handle 40 to housing 20 such that movable handle 30 and trigger 72 are not coupled about the save pivot pin 48 but, rather, are coupled about spaced-apart pivot pins 48', 48, respectively. Further still, movable handle 40 and trigger 72 may be pivotably coupled about the same pivot pin, pivot pin 48', at the location of pivot apertures 23' rather than pivot apertures 23. Longitudinal track 24 is configured to guide translation of drive assembly 140 relative to housing 20. Pivot bosses 25 extend inwardly into housing 20 and are configured to pivotably couple linkage 76 of trigger assembly 70 to housing 20. Lower leg 163 of torsion spring 160 of drive assembly 140 is configured to abut block 26 under bias to bias movable handle 40 towards the initial position, as detailed below.

Energy activation assembly 190 includes a depressible button 192 that is mechanically coupled to a switch 194 mounted within a bay 29 defined within fixed handle portion 28 of housing 20 and is engageable by a button activation post 196 extending proximally from a proximal side of movable handle 40 upon movement of movable handle 40 to the activated position, as detailed below. Switch 194 is configured to electrically communicate with end effector assembly 100 and the generator (not shown) via suitable electrical wiring, e.g., leads 131a, 131b (FIG. 31A), extending through housing 20, shaft 80, and/or electrosurgical cable 200 to enable energy to be supplied from the generator (not shown) to end effector assembly 100 upon activation of switch 194.

Continuing with reference to FIGS. 1-3, handle assembly 30 includes a movable handle 40 that is movable relative to fixed handle portion 28 of housing 20 between an initial position, a compressed position, and an activated position, as explained in greater detail below, to impart movement of jaw members 110, 120 of end effector assembly 100 between a spaced-apart position and an approximated position for grasping tissue therebetween and for initiating the supply of energy to end effector assembly 100 for treating grasped tissue. Movable handle 40 and trigger 72 of trigger assembly 70 are ergonomically configured to facilitate manipulation and operation of instrument 10. Movable handle 40, more specifically, defines a grasping portion 42 having an arcuate segment 43 and an elongated proximal leg 44 that extends from arcuate segment 43 the length of fixed handle portion 28 of housing 20. Arcuate segment 43 culminates in a distal tail 45 and defines a sufficient diameter so as to operably receive a user's finger between distal tail 45 and proximal leg 44. Arcuate segment 43 further defines a convex surface 46. Trigger 72, more specifically, defines an abutting surface 73 that abuts convex surface 46 of arcuate segment 43 of movable handle 40 and is complementarily contoured such that, in the initial position of movable handle 40 and the un-actuated position of trigger 72, pinch points between trigger 72 and movable handle 40 are eliminated. Further, trigger 72 surrounds the exposed part of flange portion 47 of movable handle 40 to eliminate pinch points therebetween.

Figure 27:
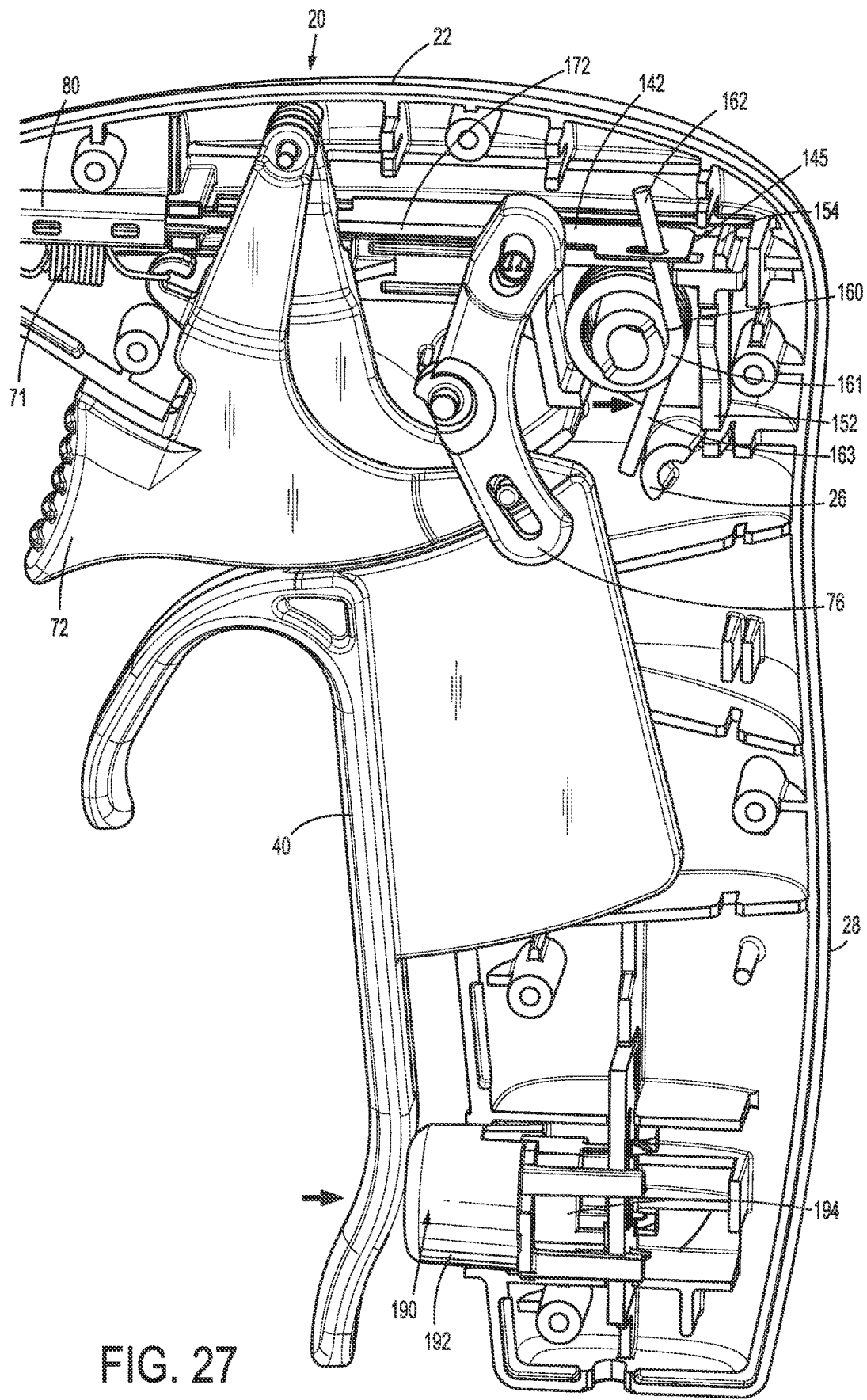
FIG. 27 is a perspective view of the proximal end of the surgical instrument of FIG. 1 with the movable handle disposed in an activated position and a portion of the housing removed to illustrate the internal components thereof.

Movable handle 40, as noted above, includes grasping portion 42, which extends from housing 20 adjacent fixed handle portion 28, and flange portion 47, which extends upwardly into housing 20. Flange portion 47 is pivotably coupled within housing 20 at the free end of flange portion 47 via pivot pin 48. Pivot pin 48 is engaged within and extends between pivot apertures 23 of housing 20 to permit movable handle 40 to pivot about pivot pin 48 and relative to housing 20 between the initial position (FIGS. 1 and 2), the compressed position (FIG. 22), and the activated position (FIG. 27). Flange portion 47 of movable handle 40 further includes a cut-out 49 defined therein and an engagement bulge 51 protruding therefrom. Cut-out 49 is configured to slidably receive drive plate 142 of drive assembly 140 and knife plate 172 of knife assembly 170. Engagement bulge 51 is configured to operably engage flange portion 47 of movable handle 40 with slider assembly 150 of drive assembly 140, as detailed below.

Referring to FIGS. 5-10, drive assembly 140 includes drive plate 142 and slider assembly 150. Drive plate 142 extends distally from housing 20 and through shaft 80 to operably engage end effector assembly 100 such that, as detailed below, translation of drive plate 142 through shaft 80 and relative to end effector assembly 100 pivots jaw members 110, 120 of end effector assembly 100 between the spaced-apart and approximated positions.

Slider assembly 150 operably couples engagement bulge 51 of flange portion 47 of movable handle 40 with drive plate 142 such that pivoting of movable handle 40 between the initial position and the compressed position pivots jaw members 110, 120 of end effector assembly 100 between the spaced-apart and approximated positions, while ensuring application of an appropriate closure force or closure force within an appropriate closure force range to tissue grasped between jaw members 110, 120 in the approximated position thereof.

Slider assembly 150 includes a proximal housing 152, a distal extension 156 extending distally from proximal housing 152, a mandrel 158 disposed at the distal end of distal extension 156, and a torsion spring 160 operably coupled to proximal housing 152. Proximal housing 152 includes a post 153 configured to receive body 161 of torsion spring 160 thereabout and open upper and lower portions configured to permit passage of the upper and lower legs 162, 163, respectively, of torsion spring 160 therethrough. Lower leg 163 extends downwardly from proximal housing 152 and is positioned to abut block 26 (which may be configured as a half-moon boss) of housing 20, thereby biasing slider assembly 150 distally and, thus, movable handle 40 towards the initial position. Torsion spring 160 remains tensioned in the initial position of movable handle 40 such that a pre-load on drive assembly 140 is maintained. Proximal housing 152 further includes an abutment rib 154 disposed on an upper surface thereof, and a longitudinal flange 155 slidably received within longitudinal track 24 of housing 20.

Continuing with reference to FIGS. 5-10, mandrel 158 is disposed at the distal end of distal extension 156 and defines a channel 159 configured to receive engagement bulge 51 of flange portion 47 of movable handle 40. As a result of this configuration, upon pivoting of movable handle 40 between the initial, compressed, and activated positions, engagement bulge 51 is urged into contact with one of the walls of mandrel 156 to thereby translate slider assembly 150 within housing 20.

Drive plate 142 includes a flange 143 and a slot 144 towards the proximal end thereof and a cam pin aperture 147 and a mouth 149 towards the distal end thereof. Slot 144 is configured to receive upper leg 162 of torsion spring 160 therethrough such that translation of upper leg 162 of torsion spring 160 relative to housing 20 effects translation of drive plate 142 relative to housing 20. Flange 143 is slidably disposed on an upper surface of proximal housing 152 and defines a proximal edge 145 configured to abut abutment rib 154 of proximal housing 152 in a proximal-most position of drive plate 142 relative to slider assembly 150 to inhibit further proximal movement of drive plate 142 relative to slider assembly 150.

Drive plate 142 extends distally from housing 20 and through shaft 80 to operably engage end effector assembly 100. Drive plate 142 is oriented similarly to shaft 80, such that the width of drive plate 142 extends along the width dimension of shaft 80. Drive plate 142 further defines a track edge 146 extending along a portion of each longitudinal side thereof. Track edges 146 are configured to slidably receive knife plate 172. A knife guide 148 is pinned to drive plate 142 towards the distal end thereof to define a channel configured to slidably receive and guide translation of knife blade 174. Knife guide 148 also provides further stability to cam pin 105. Cam-pin aperture 147 is configured to receive cam pin 105 of end effector assembly 100, while mouth 149 is configured to receive pivot pin 103 of end effector assembly 100.

Referring to FIGS. 2-12, trigger assembly 70, as mentioned above, is operably coupled to knife assembly 170 to enable selective translation of knife blade 174 of knife assembly 170 relative to end effector assembly 100. Trigger assembly 70 includes trigger 72 and a linkage 76. Trigger 72, as detailed above, includes an abutting surface 73 defined on a grasping portion 74 thereof. Trigger 72 further includes a pivot extension 75a extending upwardly from grasping portion 74 and a proximal extension 75b extending proximally from grasping portion 74. Pivot extension 75a of trigger 72 is pivotably coupled to housing 20 via pivot pin 48. Proximal extension 75b of trigger 72 includes a post 75c that is received within lower end cam slot 77c of linkage 76 to operably couple trigger 72 to linkage 76. A biasing member 71 is coupled between housing 20 and trigger 72 to bias trigger 72 distally towards an un-actuated position (FIG. 2).

Linkage 76 serves to operably couple trigger 72 with knife assembly 170 such that pivoting of trigger 72 from the un-actuated position to the actuated position advances knife blade 174 (FIGS. 10-12) between jaw members 110, 120 of end effector assembly 100 to cut tissue grasped therebetween. Linkage 76 includes an apex 77a pointing in a distal direction and upper and lower end cam slots 77b, 77c, respectively. Apex 77a includes a peg 77d that is configured for receipt within pivot boss 25 of housing 20 to pivotably couple linkage 76 relative to housing 20 about apex 77a. A coupling tube 78 engaged with knife plate 172 of knife assembly 170 is configured for receipt within upper end cam slot 77b to operably couple linkage 76 to knife plate 172. More specifically, coupling tube 78 is configured to receive legs 173, which extend transversely from the proximal end of knife plate 172, in snap-fit engagement therein (see FIG. 9). As noted above, post 75*c* of proximal extension 75*b* of trigger 72 is configured for receipt within lower end cam slot 77*c* of linkage 76.

As a result of the above-detailed configuration, Pivoting of trigger 72 between the un-actuated and actuated positions urges linkage 76 to pivot relative to housing 20 such that coupling tube 78 is urged to translate longitudinally within and relative to housing 20. As legs 173 of knife plate 172 are engaged with coupling tube 78, such longitudinal translation of coupling tube 78 is imparted to knife plate 172 for translating knife blade 174 (FIGS. 10-12) from a retracted position to an extended position relative to jaw members 110, 120 of end effector assembly 100.

Linkage 76 of trigger assembly 70 further includes a lockout peg 79 extending transversely from linkage 76 and positioned between apex 77*a* and lower end cam slot 77*c*. In the initial position of movable handle 40, proximal housing 152 of slider assembly 150 is disposed in a more distal position so as to interfere with the movement path of lockout peg 79 (see FIG. 21), thus inhibiting actuation of trigger 72 when movable handle 40 is disposed in its initial position. Upon movement of movable handle 40 sufficiently towards the compressed position, proximal housing 152 of slider assembly 150 is moved proximally out of the movement path of lockout peg 79 (see FIG. 24), permitting rotation of linkage 76 and, thus, actuation of trigger 72.

Figure 10:
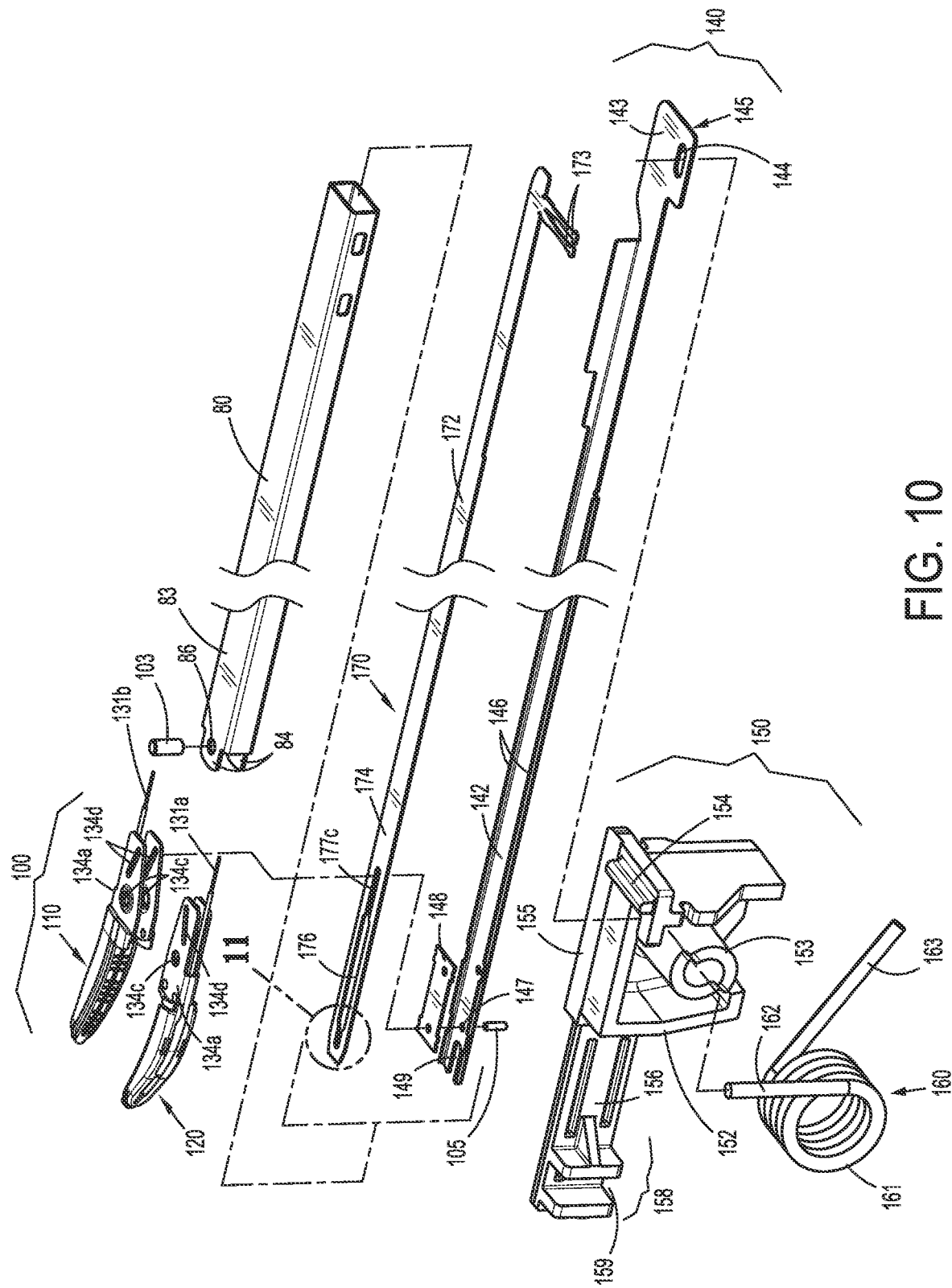
FIG. 10 is a rear, perspective, exploded view of the drive assembly, shaft, knife, and end effector assembly of the surgical instrument of FIG. 1.

With reference to FIGS. 8-12, knife assembly 170, as noted above, includes a knife plate 172 defining legs 173 extending transversely therefrom towards the proximal end thereof. Knife plate 172 extends distally through housing 20 and shaft 80 atop drive plate 142 and is slidably engaged therewith via receipt of each side of knife plate 172 within track edges 146 of drive plate 142. Knife assembly 170 further includes knife blade 174 integrally formed with or otherwise engaged to knife plate 172 and extending distally therefrom. Knife blade 174 is slidably disposed within the channel defined between drive plate 142 and knife guide 148 and defines a serrated distal cutting edge 175 (see FIGS. 11 and 12) to facilitate cutting tissue grasped between jaw members 110, 120 of end effector assembly 100. Knife blade 174 further defines an elongated opening 176 extending longitudinally therethrough. Elongated opening 176 permits knife blade 174 to be slidably disposed about pivot pin 103 and cam pin 105. More specifically, elongated opening 176 defines a first portion 177*a*, a second portion 177*b*, and a third portion 177*c* (FIG. 10). First portion 177*a* has a first width configured to slidably receive pivot pin 103 and cam pin 105. Second portion 177*b* extends distally from first portion 177*a*, has a second width, and is configured to facilitate compliance of knife blade 174 as it is translated through the curved end effector assembly 100 (FIG. 13). Third portion 177*c* (FIG. 10) extends proximally from first portion 177*a* and has a third width (equal to or different from the second width) configured to slidably receive cam pin 105 but sufficiently small to inhibit receipt of the larger-diameter pivot pin 103 therein.

Figure 11:
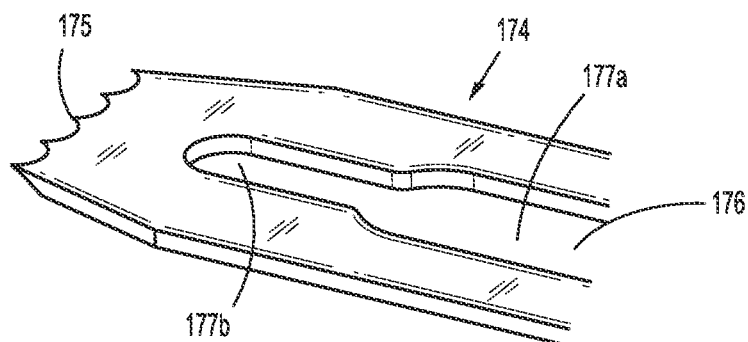
FIG. 11 is an enlarged, perspective view of the area of detail indicated as "11" in FIG. 10.
Figure 12:
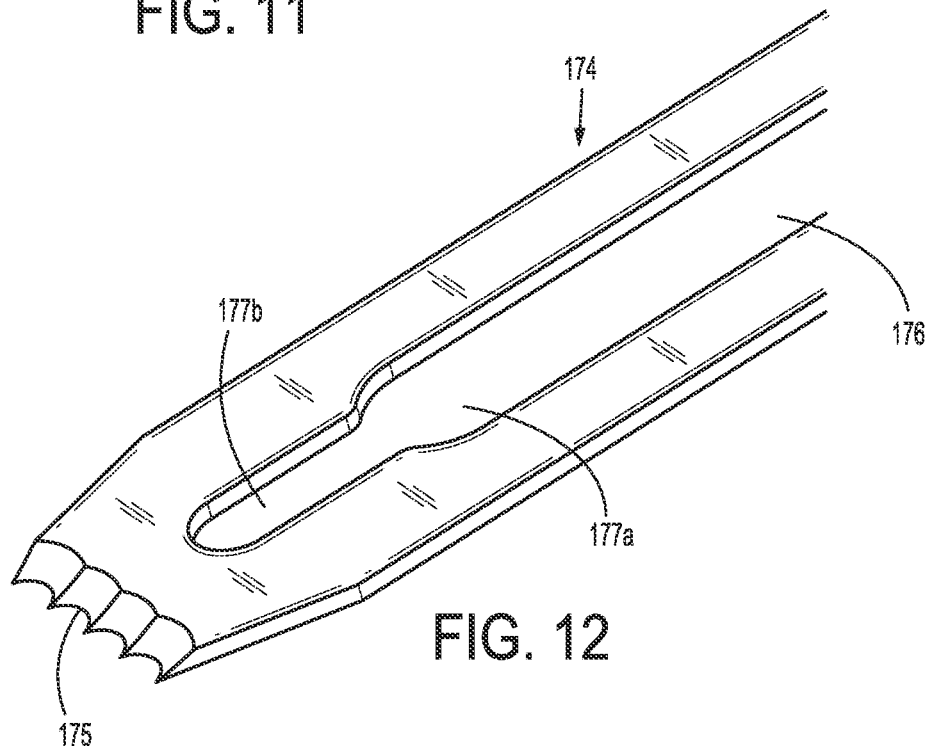
FIG. 12 is another enlarged, perspective view of the distal end of the knife blade of the surgical instrument of FIG. 1.
Figure 12:
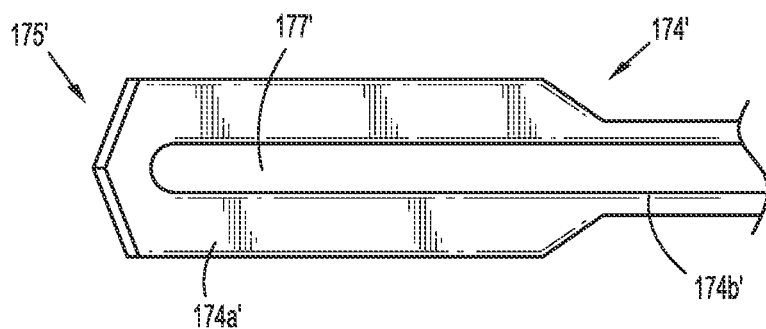
Figure 13:
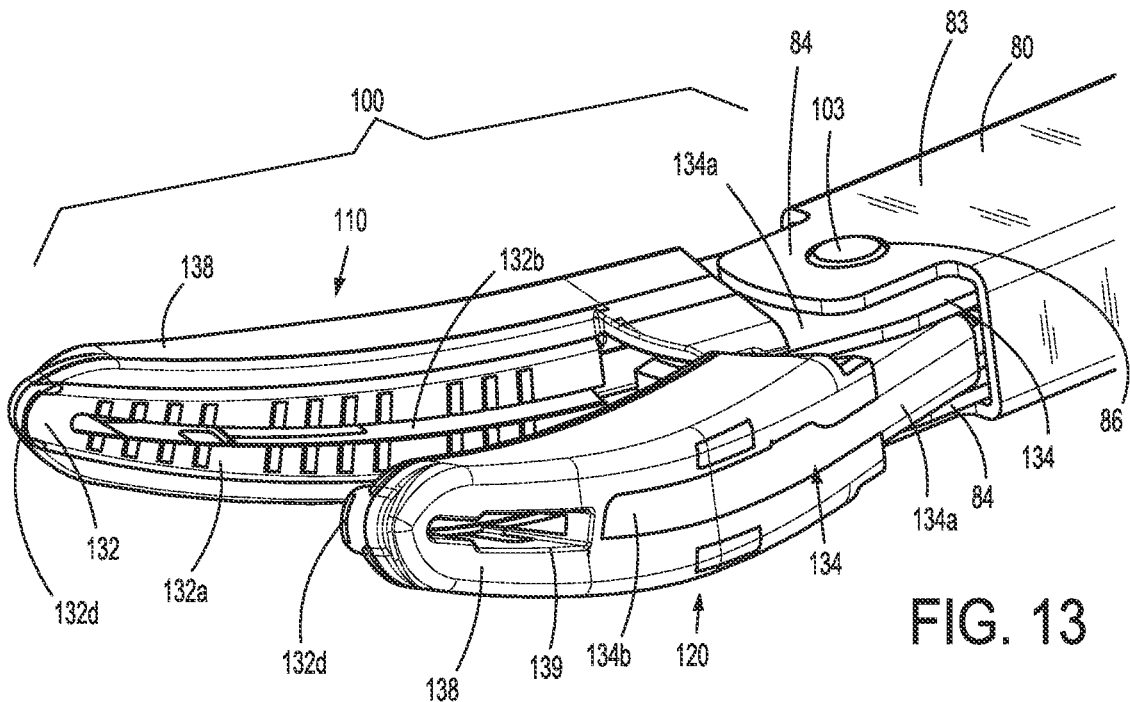
FIG. 13 is a perspective view of the distal end of the surgical instrument of FIG. 1 with the jaw members disposed in the spaced-apart position.
Figure 14:
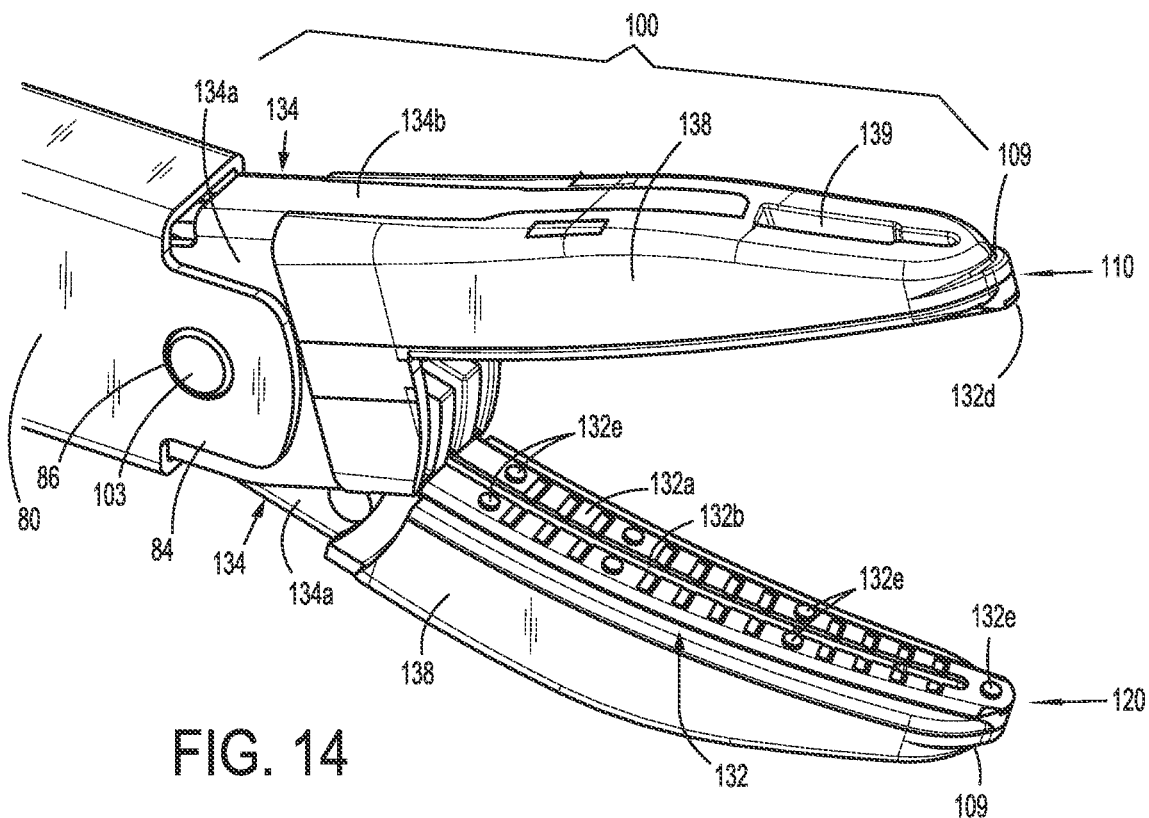
FIG. 14 is another perspective view of the distal end of the surgical instrument of FIG. 1 with the jaw members disposed in the spaced-apart position.
Figure 19:
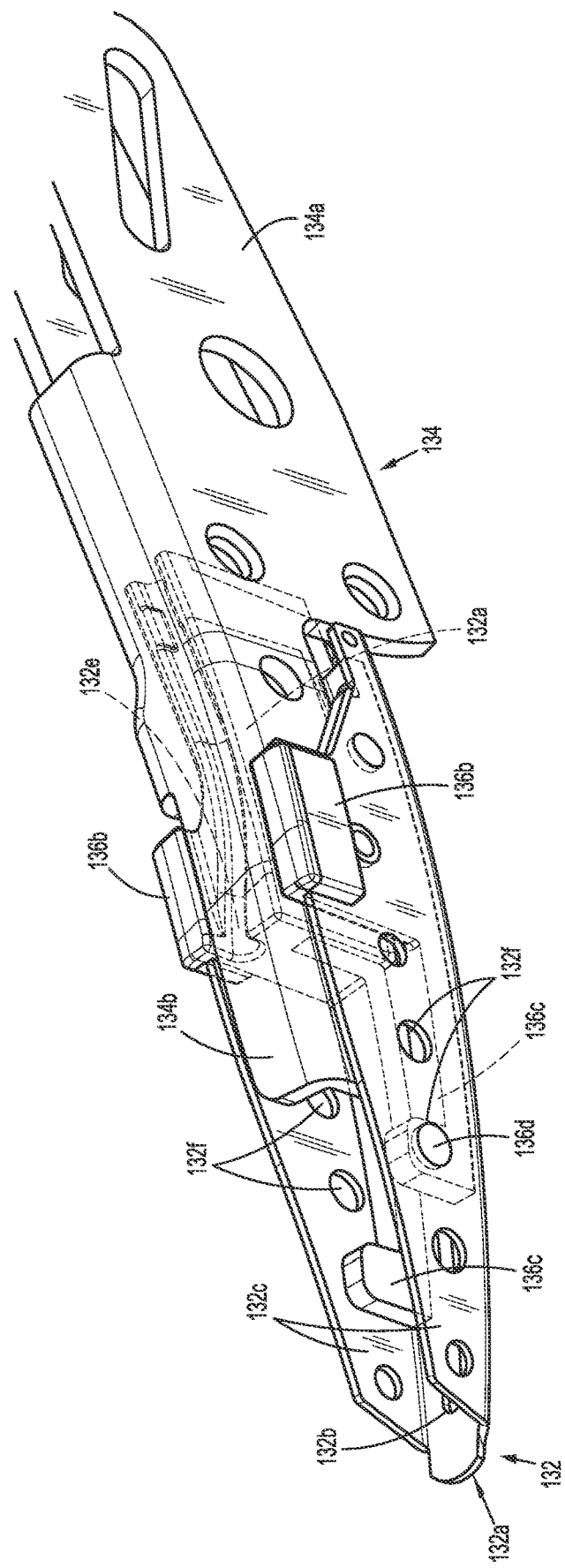
FIG. 19 is a perspective view of the electrically-conductive plate, jaw frame, and overmolded spacer of one of the jaw members of the surgical instrument of FIG. 1.

Turning to FIG. 12', another knife blade 174' configured for use with instrument 10 is provided. To the extent consistent, and unless contradicted hereinbelow, knife blade 174' may include similar features, functions, and connections to the other components of instrument 10 as those detailed herein with respect to knife blade 174 (FIGS. 11 and 12). Knife blade 174' defines a heightened distal portion 174*a'* and a relatively shorter body portion 174*b'*. The heightened distal portion 174*a'* of knife blade 174' inhibits tissue from being positioned above or below knife blade 174' as knife blade 174' is translating through end effector assembly 100 (FIG. 14), while the shorter body portion 174*b'* of knife blade 174' maintains a low profile configuration within shaft 80 (FIG. 14). Knife blade 174' further defines an elongated opening 177' therethrough that, although shown as having a generally constant width, may alternatively be configured similar to elongated opening 176 of knife blade 174 (FIGS. 11 and 12).

The distal cutting edge 175' of knife blade 174' defines a dual rake configuration, wherein the edge portions of distal cutting edge 175' extend distally and angle inwardly towards one another, ultimately culminating in a point that is generally centered about a longitudinal axis of knife blade 174' and positioned distally of heightened distal portion 174*a'* of knife blade 174'. This configuration of distal cutting edge 175' has been found to: reduce the force required to advance knife blade 174' through tissue due to its aerodynamic configuration; enable cutting further towards the distal tip of end effector assembly 100 (FIG. 14) by virtue of the inwardly and distally extending cutting edge portions of distal cutting edge 175'; and enable a reduction in overall jaw height for either or both of the jaw members 110, 120 without restricting knife performance.

With reference to FIGS. 10 and 13-19, as mentioned above, end effector assembly 100 is operably supported at the distal end of shaft 80 and includes opposing jaw members 110, 120 pivotably coupled to one another and movable relative to one another and shaft 80 between a spaced-apart position and an approximated position for grasping tissue therebetween. Jaw members 110, 120 are similar to one another, unless otherwise detailed hereinbelow. Thus, common features to both jaw member 110 and jaw member 120 may not be described and/or illustrated with respect to each of jaw members 110, 120.

Each jaw member 110, 120 includes an electrically-conductive plate 132, a jaw frame 134, a spacer 136, and an outer housing 138, each of which is detailed below. Jaw members 110, 120 define curved configurations, wherein jaw members 110, 120 bend upwardly from a longitudinal axis of shaft 80, e.g., towards the upper, larger width dimension wall of shaft 80. This configuration facilitates use of instrument 10 in tonsillectomy and adenoidectomy procedures as well as other surgical procedures and allows for increased visualization of the surgical site in these and other procedures.

The electrically-conductive plate 132 of each jaw member 110, 120 defines a generally planar tissue-contacting surface 132*a*, an elongated knife slot 132*b* extending through the respective tissue-contacting surface 132*a*, a pair of legs 132*c* extending downwardly from each side of the respective tissue-contacting surface 132*a*, and a distal edge 132*d* disposed at the distal end of the respective tissue-contacting surface 132*a*.

The tissue-contacting surface 132*a* of jaw member 110 and/or jaw member 120 may include a plurality of stop members 132*e* disposed thereon. Stop members 132*e* may be constructed of a heat-resistant ceramic, a non-conductive plastic, an electrically conductive material isolated from the respective tissue-contacting surface 132*a*, or any other suitable material, and/or may be deposited, molded, inserted through apertures, or otherwise formed on the tissue-contacting surface 132*a* of jaw member 110 and/or jaw member 120. Legs 132*c* of electrically-conductive plates 132 each define a plurality of apertures 132*f* therethrough.

Jaw frames 134 of jaw members 110, 120 each include a pair of spaced-apart proximal flanges 134*a* and a distal jaw support 134*b* extending distally from the proximal flanges 134a. Proximal flanges 134a of jaw member 110 are spaced-apart further than proximal flanges 134a of jaw member 120 so as to allow proximal flanges 134a of jaw member 120 to be positioned between proximal flanges 134a of jaw member 110 during assembly. Further, the proximal flanges 134a of each pair define aligned pivot apertures 134c and aligned cam slots 134d. Pivot pin 103 of end effector assembly 100 is configured for vertical insertion through apertures 86 of clevis members 84 of shaft 80 and pivot apertures 13c to pivotably couple jaw members 110, 120 to shaft 80 and one another. Pivot pin 103 is further configured to at least partially enter mouth 149 of drive plate 142 to permit drive plate 142 to slide further distally relative to end effector assembly 100 to a position wherein mouth 149 of drive plate 142 at least partially surrounds pivot pin 103.

Continuing with reference to FIGS. 10 and 13-19, the cam slots 134d of proximal flanges 134a of jaw member 110 are oppositely angled relative to the cam slots 134d of proximal flanges 134a of jaw member 120. Cam pin 105 of end effector assembly 100 is configured for insertion through each cam slot 134d as well as cam-pin aperture 147 of drive plate 142 to operable couple drive plate 142 with jaw members 110, 120 such that translation of drive plate 142 relative to jaw members 110, 120 pivots jaw members 110, 120 about pivot pin 103 and relative to one another and shaft 80 between the spaced-apart and approximated positions.

Distal jaw supports 134b of jaw frames 134 of jaw members 110, 120 define generally "L-shaped" configurations and are configured to support electrically-conductive plates 132, spacers 136, and outer housings 138 of jaw members 110, 120. However, distal jaw supports 134b only extend a length of about 50% to about 75% of the length of jaw members 110, 120.

Spacers 136 of jaw members 110, 120 define generally "M-shaped" configurations, are formed from electrically-insulative materials, and are overmolded onto distal jaw supports 134b during a first overmold, although other manufacturing processes are also contemplated. Spacers 136 are positioned to electrically-isolate electrically-conductive plates 132 from one another and from jaw frames 134. Spacers 136 each define a body 136a, a pair of wings 136b surrounding body 136a, and a pair of support arms 136c extending distally from the corresponding body 136a. The bodies 136a of spacers 136 define tunnels 136e for passage of lead wires 131a, 131b therethrough to electrically couple electrically-conductive plates 132 to switch 194 of energy activation assembly 190 (FIGS. 1 and 2) and the generator (not shown). Wings 136b capture the legs 132c of electrically-conductive plates 132.

Support arms 136c of spacers 136b extend along the legs 132c of electrically-conductive plate 132 to provide structural support thereto, and may define equal or different lengths. For example, due to the curved configuration of jaw members 110, 120, additional support adjacent the interior or concave side may be required and, thus, the support arm 136c adjacent thereto may be longer than the support arm 136c adjacent the outer or convex side. However, other configurations are also contemplated. Support arms 136c further include protrusions 136d that extend therefrom through some but not all of the apertures 132f defined along the length of legs 132c of electrically-conductive plates 132 to secure support arms 136c thereto and reinforce the structural stability thereof. The above-detailed configuration of support arms 136c inhibits legs 132c of electrically-conductive plates 132 from bending, buckling, and/or becoming wave-shaped under the forces applied thereto during overmolding, assembly, and/or use.

Outer housings 138 are formed about jaw members 110, 120 via a second overmold process, such that each outer housing 138 partially encloses respective jaw members 110, 120 with the exception of a portion of the distal jaw support 113b, 123b thereof and the tissue-contacting surface 112a, 122a thereof, which remain exposed. Further, the apertures 132f defined through legs 132c of electrically-conductive plates 132 that are not occupied by protrusions 136d of arms 136c of spacers 136 are filled via portions of outer housing 138 during the second overmold process to ensure that electrically-conductive plates 132 are secured in position. Outer housings 138 also define windows 139 that align with and communicate with the knife slots 132b of electrically-conductive plates 132 so as to define an opening through the distal portions of jaw members 110, 120 transversely from the tissue-contacting surfaces 132a of electrically-conductive plates 132 to the outer surfaces of outer housings 138.

With outer housings 138 formed about jaw members 110, 120, respectively, distal edges 132d of electrically-conductive plates 132 overlap the distal ends of outer housings 138 such that distal edges 132d can be utilized to pinch tissue therebetween. Further, outer housings 138 each define cutouts on the outer surfaces thereof towards the distal ends thereof that form shelves 109 on the outer surfaces of jaw members 110, 120 to facilitate poking and spreading tissue.

Figure 20:
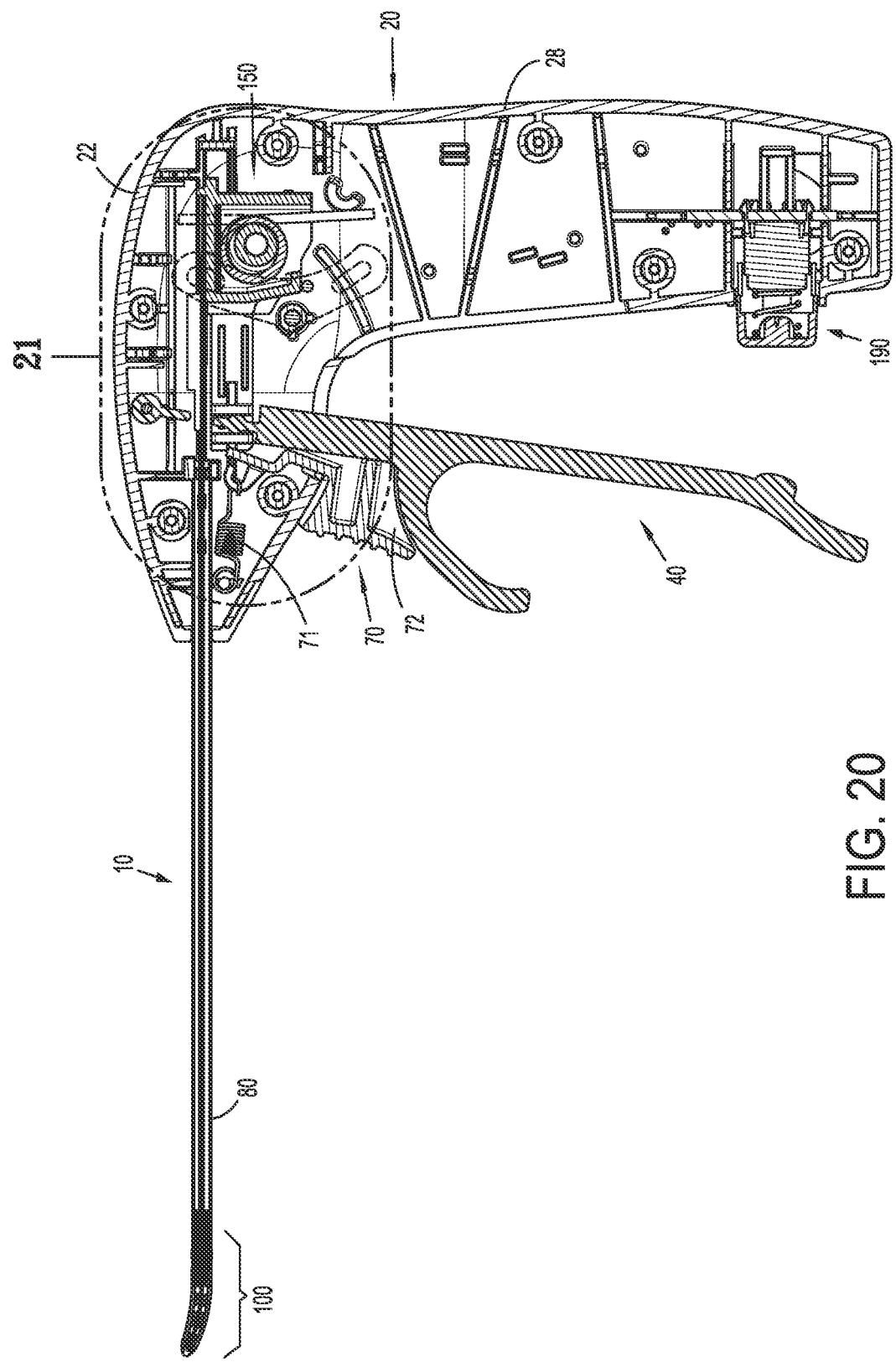
FIG. 20 is a longitudinal, cross-sectional view of the surgical instrument of FIG. 1 with the surgical instrument disposed in an initial position.
Figure 21:
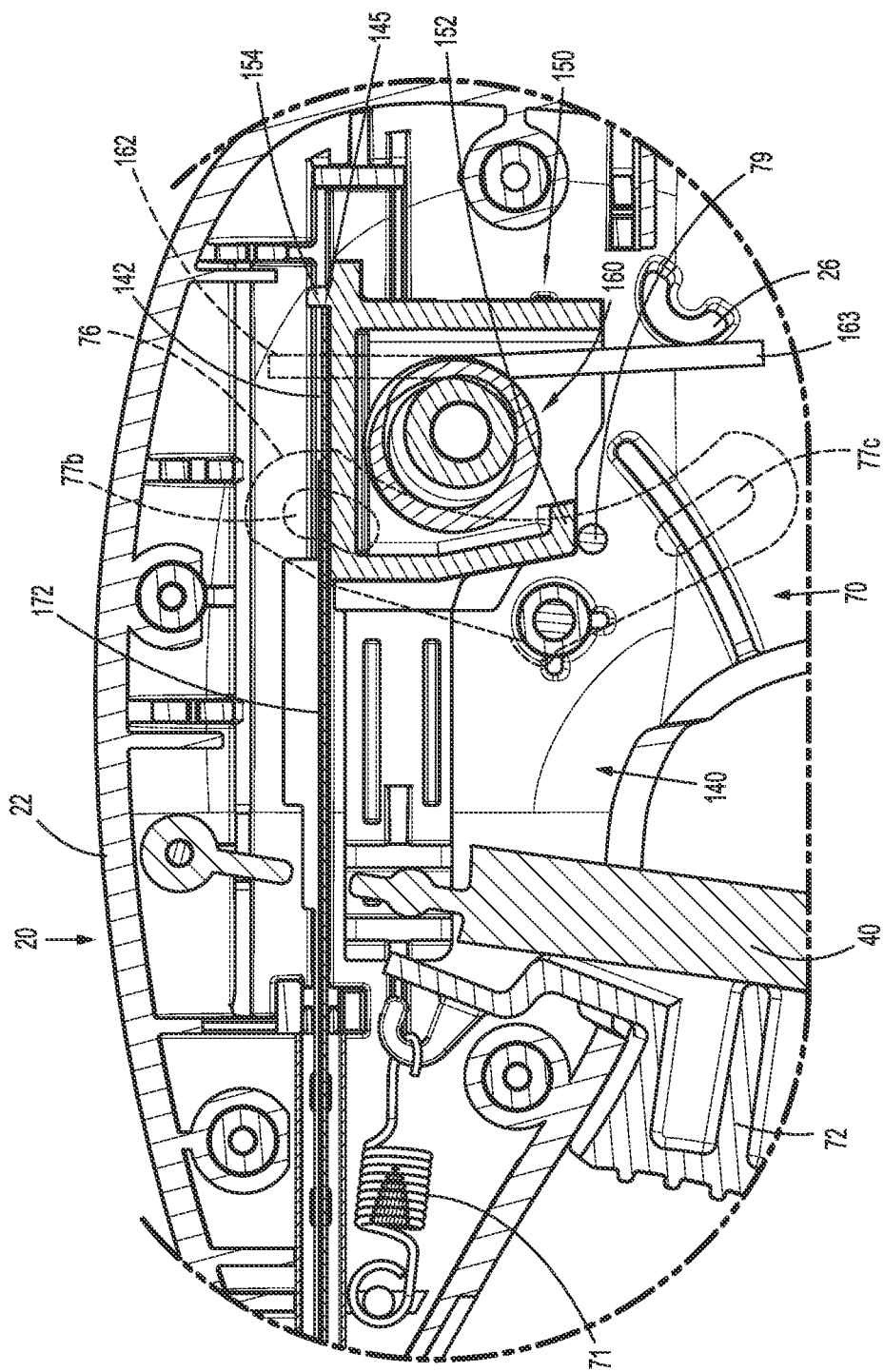
FIG. 21 is an enlarged, side, cross-sectional view of the area of detail indicated as "21" in FIG. 20.
Figure 24:
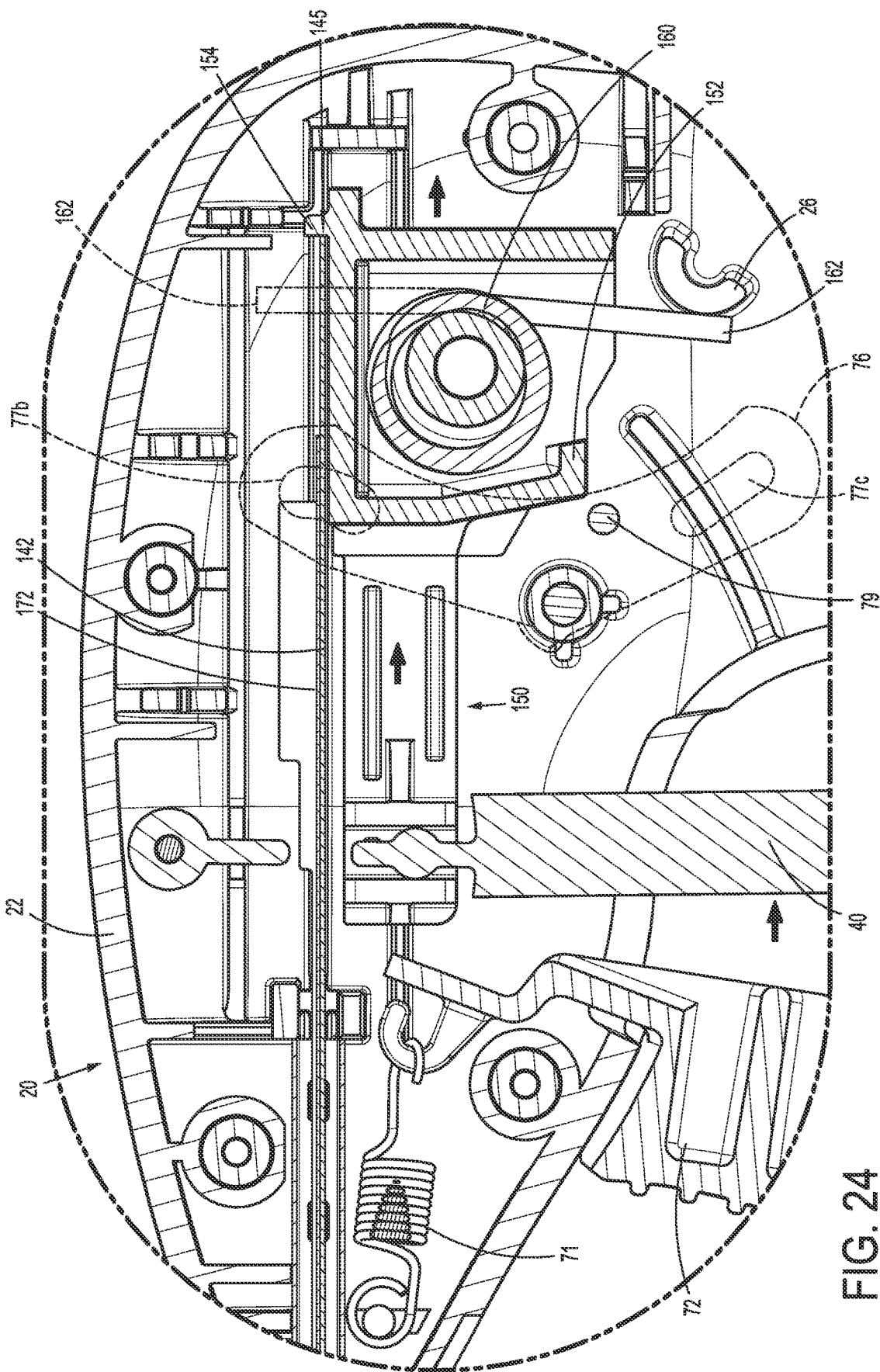
FIG. 24 is an enlarged, longitudinal, cross-sectional view of the internal components of the housing of the surgical instrument of FIG. 1, wherein the movable handle is disposed in the compressed position.
Figure 25:
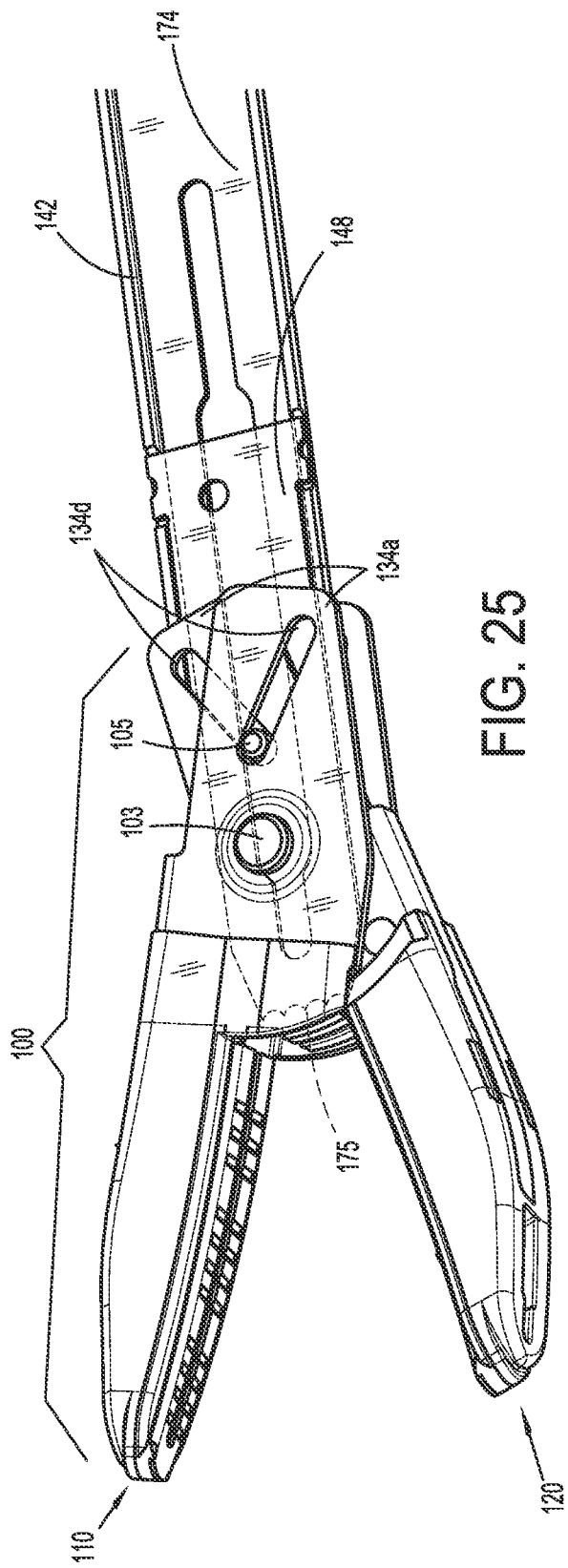
FIG. 25 is a perspective view of the distal end of the drive, knife, and end effector assemblies of the surgical instrument of FIG. 1, with the jaw members disposed in the spaced-apart position.
Figure 26:
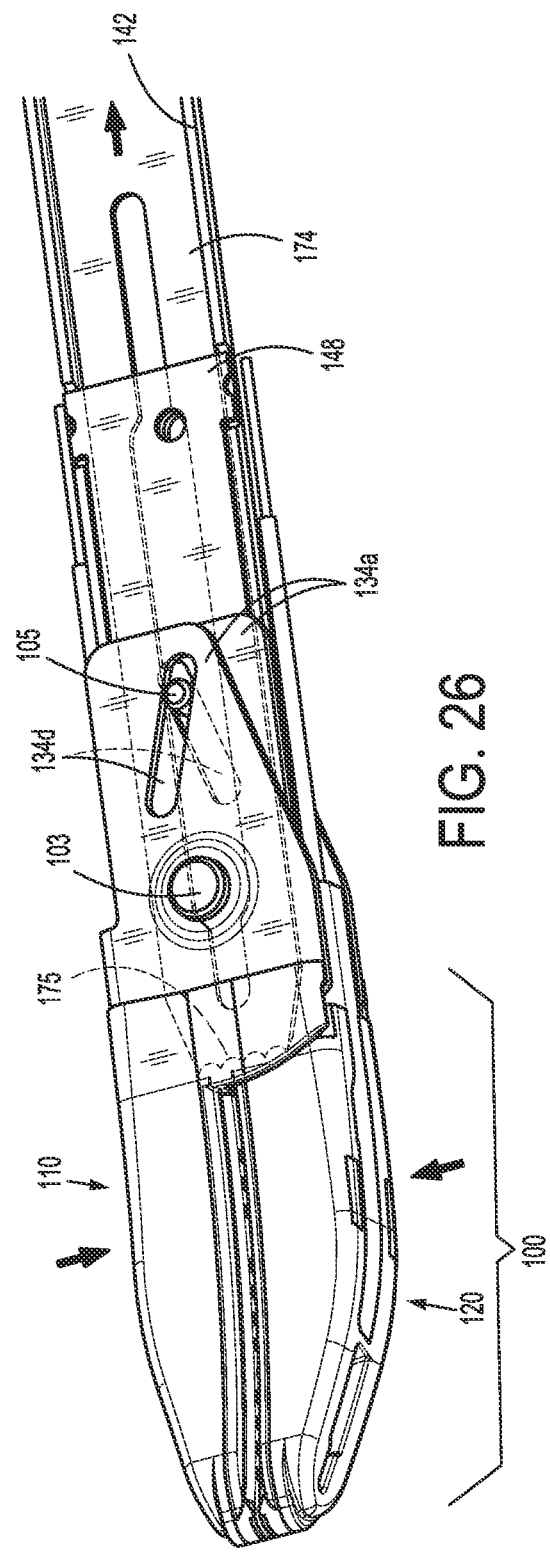
FIG. 26 is a perspective view of the distal end of the drive, knife, and end effector assemblies of the surgical instrument of FIG. 1, with the jaw members disposed in the approximated position.

Turning now to FIGS. 20-30, the use and operation of instrument 10 is described. Initially, as illustrated in FIGS. 20, 21, and 25, movable handle 40 is biased towards the initial position by the abutment of lower leg 163 of torsion spring 160 with block 26 of housing 20. With movable handle 40 in the initial position, slider assembly 150 is likewise disposed in a distal-most position. With slider assembly 150 disposed in its distal-most position, upper leg 162 of torsion spring 160 retains drive plate 142 in a distal-most position with the proximal edge 145 of drive plate 142 disposed in abutment with abutment rib 154 of proximal housing 152 of slider assembly 150. In the distal-most position of drive plate 142, drive plate 142 and knife guide 148 maintain cam pin 105 at the distal ends of oppositely-angled cam slots 134d of proximal flanges 134a of jaw members 110, 120 to thereby maintain jaw members 110, 120 in the spaced-apart position (see FIG. 25).

At this point, with continued reference to FIGS. 20, 21, and 25, trigger 72 is disposed in the un-actuated position, wherein trigger 72 is in a distal-most position under the bias of biasing member 71 such that upper end cam slot 77b of linkage 76 is disposed in a proximal-most position while lower end cam slot 77c of linkage 76 is disposed in a distal-most position. Thus, knife plate 172 is disposed in a proximal-most position, corresponding to a retracted position of knife blade 174, wherein knife blade 174 is disposed between proximal flanges 134a of jaw frames 134 of jaw members 110, 120 but does not extend distally therefrom. Further, with movable handle 40 disposed in its initial position, proximal housing 152 of slider assembly 150 is disposed in the movement path of lockout peg 79 of linkage 76, inhibiting rotation of linkage 76 and, thus, inhibiting movement of trigger 72 from the un-actuated position to the actuated position. As such, knife blade 174 is inhibited from being deployed when jaw members 110, 120 are disposed in the spaced-apart position.

Figure 22:
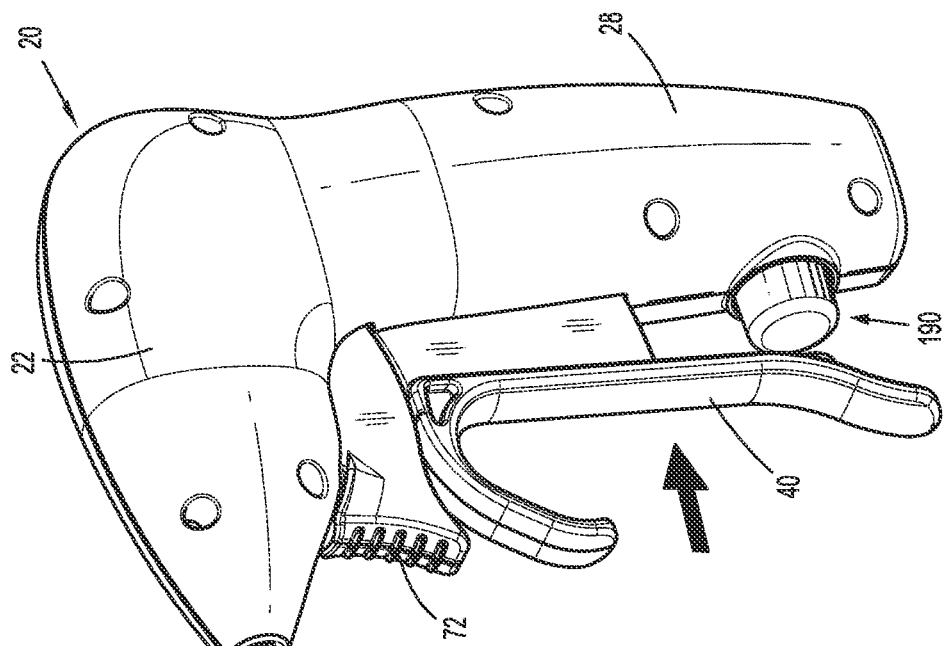
FIG. 22 is a perspective view of the surgical instrument of FIG. 1 with the movable handle disposed in a compressed position and, accordingly, the jaw members disposed in the approximated position.
Figure 23:
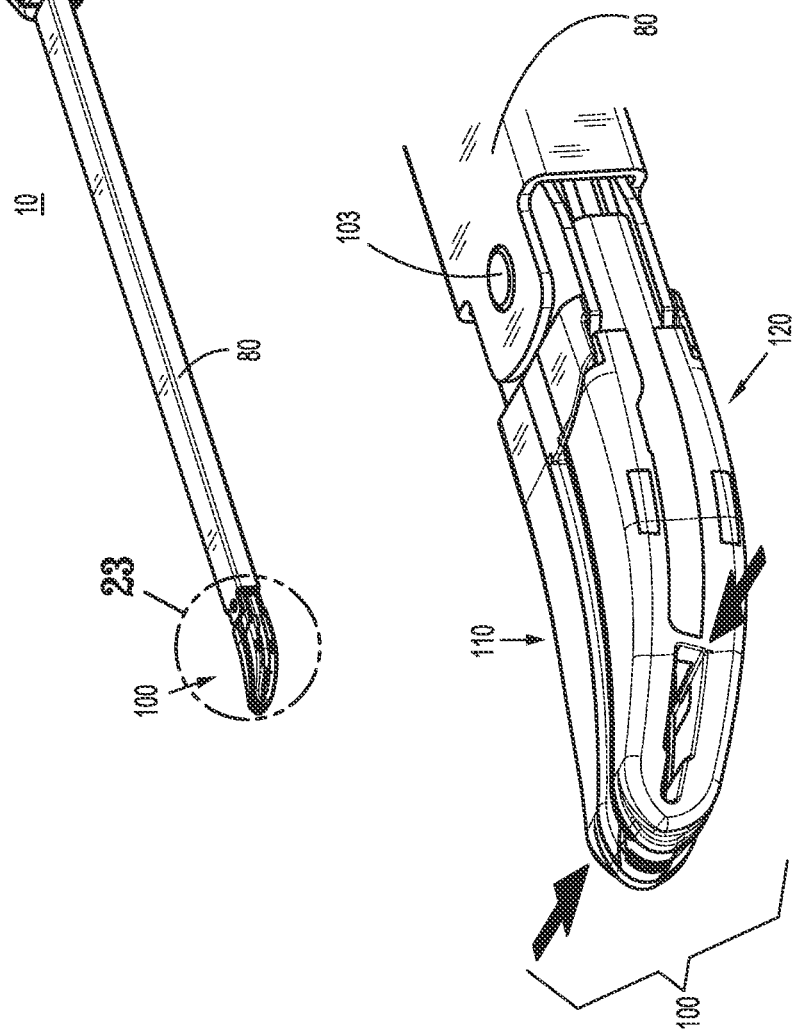
FIG. 23 is an enlarged, perspective view of the area of detail indicated as "23" in FIG. 22.

With additional reference to FIGS. 22-24, and 26, in order to move jaw members 110, 120 to the approximated position to grasp tissue therebetween, movable handle 40 is pulled proximally towards fixed handle portion 28 of housing 20 from the initial position to the compressed position (FIGS. 22 and 24). Upon movement of movable handle 40 to the compressed position, movable handle 40 urges slider assembly 150 proximally through housing 20. Torsion spring 160, in an initial, less-tensioned state, is translated proximally together with slider assembly 150 such that upper leg 162 of torsion spring 160 pulls drive plate 142 proximally in connection with the proximal translation of slider assembly 150. In other words, at this point, slider assembly 150 and drive plate 142 move in concert with one another. As drive plate 142 is pulled proximally, cam pin 105 is pulled proximally through cam slots 134*d* of proximal flanges 134*a* of jaw members 110, 120 such that jaw members 110, 120 are pivoted from the spaced-apart position to the approximated position (FIGS. 23 and 26) to grasp tissue therebetween.

Referring also to FIG. 27, in order to apply energy to tissue grasped between jaw members 110, 120 to treat tissue, movable handle 40 is compressed further towards fixed handle portion 28 of housing 20 to an activation position, wherein an appropriate closure force or closure force within an appropriate range, is achieved and energy activation is initiated. As movable handle 40 is moved further proximally relative to housing 20 beyond the compressed position, an appropriate closure force or closure force within an appropriate range is imparted to tissue grasped between jaw members 110, 120 regardless of the thickness or compressibility of tissue or the position of movable handle 40. This is because, upon movement of movable handle 40 from the compressed position towards the activation position, proximal housing 152 of slider assembly 150 is translated proximally while drive plate 142 is maintained in position. In other words, upon movement of movable handle 40 from the compressed position to the activated position, proximal housing 152 and drive plate 142 no longer move in concert with one another but are decoupled to permit relative motion therebetween.

The decoupling of proximal housing 152 of slider assembly 150 and drive plate 142 to permit relative motion therebetween is provided via torsion spring 160. More specifically, upon proximal movement of movable handle 40, a first force is imparted from movable handle 40, through proximal housing 152 of slider assembly 150, body 161 of torsion spring 160, and upper leg 162 of torsion spring 160, to drive plate 142 to urge drive plate 142 in a proximal direction, while a second, opposite force acts on drive plate 142 and, thus, upper leg 162 of torsion spring 160 in a distal direction to control the amount of compression of tissue between jaw members 110, 120. Once the second, opposite force exceeds the spring force of torsion spring 160, proximal movement of proximal housing 152 no longer results in proximal movement of drive plate 142 but, rather, results in further tensioning of torsion spring 160, wherein torsion spring 160 is wound-up, absorbing the force imparted thereto from movement of movable handle 40. Thus, once this point has been reached, further proximal translation of proximal housing 152 of slider assembly 150 urges body 161 of torsion spring 160 proximally while upper leg 162 of torsion spring 160 remains in position as a result of the wind-up tensioning of torsion spring 160. With upper leg 162 of torsion spring 160 retained in position, drive plate 142 is likewise retained in position despite the proximal translation of movable handle 40. As such, an upper threshold of pressure applied to tissue grasped between jaw members 110, 120 is defined.

Referring to FIG. 27, upon achieving the activation position of movable handle 40, button activation post 196 (FIG. 1) of movable handle 40 contacts depressible button 192 sufficiently so as to depress depressible button 192 into fixed handle portion 28 of housing 20 to activate switch 194. Switch 194, as noted above, is disposed in electrical communication with the generator (not shown) and electrically-conductive plates 132 of jaw members 110, 120 (FIG. 14), such that activation of switch 194 initiates the supply of energy to electrically-conductive plates 132 (FIG. 14) to treat, e.g., coagulate, cauterize, and/or seal, tissue grasped therebetween.

Figure 28:
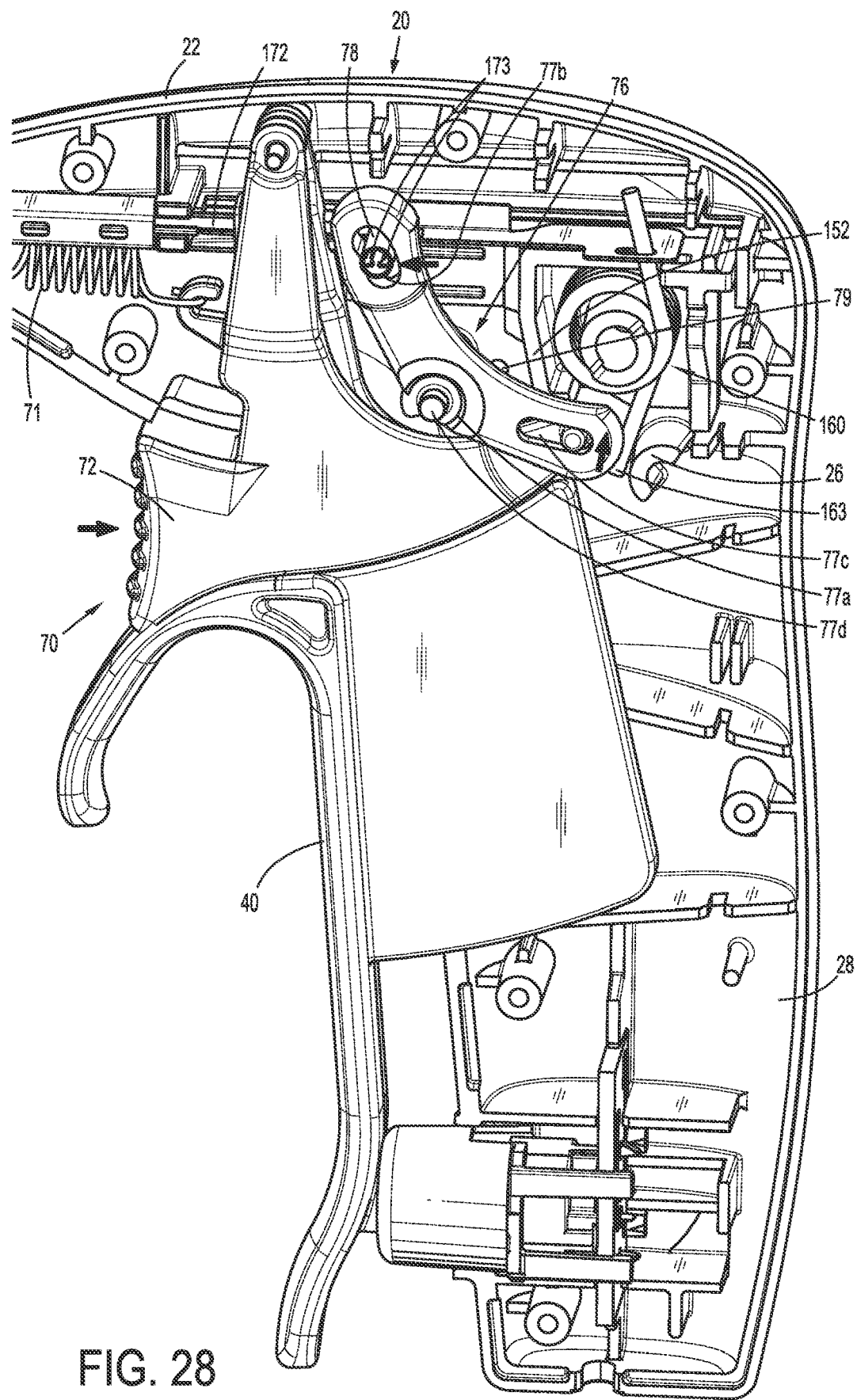
FIG. 28 is a perspective view of the proximal end of the surgical instrument of FIG. 1 with the trigger disposed in an actuated position and a portion of the housing removed to illustrate the internal components thereof.

Referring to FIGS. 28-30, once tissue has been treated or where it is only desired to cut tissue, knife blade 174 may be advanced between jaw members 110, 120 to cut tissue grasped therebetween. In order to advance knife blade 174 from the retracted position to the extended position, trigger 72 is pulled proximally against the bias of biasing member 71 from the un-actuated position to the actuated position. As trigger 72 is pulled proximally, linkage 76 is urged to pivot counter-clockwise (from the orientation illustrated in FIG. 28) such that upper end slot 77*b* of linkage 76 is moved distally. Distal movement of upper end slot 77*b* urges tube 78 to translate distally and, in turn, urges knife plate 172 to translate distally. This movement is permitted as, with movable handle 40 in or near the compressed or actuated position, proximal housing 152 is displaced relative to the movement path of lockout peg 79.

As detailed above, movement of trigger 72 from the un-actuated position to the actuated position urges knife plate 172 distally. More specifically, knife plate 172 is urged distally such that knife blade 174 is advanced distally from the retracted position to the extended position. As knife blade 174 is advanced distally, knife blade 174 extends through knife slots 132*b* defined within electrically-conductive plates 132 of jaw members 110, 120 defined by the respective knife slots 112*b*, 122*b* of electrically-conductive plates 112, 122 to cut tissue grasped between jaw members 110, 120.

Upon release, trigger 72 and knife plate 172 are returned proximally under the bias of biasing member 71 such that knife blade 174 is returned to the retracted position. Thereafter, movable handle 40 may be released, allowing movable handle 40 to return to the initial position under the bias of lower leg 163 of torsion spring 160 abutting block 26 of housing 20, thereby returning jaw members 110, 120 to the spaced-apart position and releasing the treated and/or divided tissue.

Referring generally to FIGS. 1-10, the assembly of surgical instrument 10 is detailed. Unless necessitated by the positioning of the components, e.g., wherein a second component obstructs a first components, the assembly of surgical instrument 10 need not be performed in the order detailed below. Further, it is contemplated that certain assemblies and/or components, e.g., each of the jaw members 110, 120 (the assembly of which is detailed above), be pre-assembled prior to engagement with the other components of surgical instrument 10.

The previously-assembled jaw members 110, 120 are manipulated such that the proximal flanges 134*a* of jaw member 110 receive the proximal flanges 134*a* of jaw member 120 therebetween with the pivot apertures 134*c* thereof aligned with one another. Leads 131*a*, 131*b*, which extend proximally from jaw members 110, 120, are routed proximally through shaft 80.

Knife plate 172 (including knife blade 174 at the distal end thereof) is slidably coupled to drive plate 142 via insertion of knife blade 174 between plate 142 and knife guide 148 with the longitudinal edges of knife plate 172 are slidably received within track edges 146 of drive plate 142.

Prior to or after coupling of knife plate 172 and drive plate 142, coupling tube 78 is snap-fit about legs 173 of knife plate 172.

With knife plate 172 and drive plate 142 coupled to one another, the pair is inserted through the proximal end of shaft 80 until cam pin aperture 147 of drive plate 142 and elongated opening 176 of knife blade 174 are aligned with cam slots 134d of jaw members 110, 120. Once this alignment has been achieved, cam pin 105 may be inserted therethrough to operably couple drive plate 142 with jaw members 110, 120.

With cam pin 105 operably coupling jaw members 110, 120 with drive plate 142, proximal flanges 134a of jaw members 110, 120 are inserted between clevis members 84 of shaft 80 such that pivot pin apertures 86 of shaft 80 are aligned with pivot apertures 134c of jaw members 110, 120. With apertures 134c and 86 aligned with one another, pivot pin 103 may be inserted therethrough to pivotably couple jaw members 110, 120 to shaft 80 and one another. Achieving the above insertion of cam pin 105 and/or pivot pin 103 may be facilitated using appropriate fixturing (not shown) and/or a lead pin (not shown). To secure pivot pin 103 in position, pivot pin 103 may be laser welded to the exterior of shaft 80 about the perimeter of pivot pin 103 and apertures 86 of shaft 80. Testing may be performed after welding to ensure proper pivoting of jaw members 110, 120 in response to translation of drive plate 142 and to ensure proper advancement and retraction of knife blade 174 relative to jaw members 110, 120.

In order to assemble and install drive assembly 140, torsion spring 160 is positioned within proximal housing 152 of slider assembly 150 such that post 153 of proximal housing 152 receives body 161 of torsion spring 160 with upper and lower legs 162, 163, respectively, of torsion spring 160 extending from proximal housing 152. Proximal housing 152 and/or the proximal end of drive plate 142 are then manipulated such that the proximal end of drive plate 142 is slidably supported atop proximal housing 152 with upper leg 162 of torsion spring 160 extending through slot 144 defined within drive plate 142.

The assembly thus far (end effector assembly 100, shaft 80, drive plate 142, slider assembly 150, and knife assembly 170) is positioned within one of the first or second housing components of housing 20 such that shaft 80 is fixed in position relative thereto, proximal housing 152 is slidably received within longitudinal track 24 of housing 20, and lower leg 163 of torsion spring 160 abuts a distally-facing surface of block 26 of housing 20. Leads 131a, 131b are routed around housing 20 so as not to interfere with the internal operating components thereof, are connected to activation assembly 190, and are connected to electrosurgical cable 200, which extends from housing 20.

Next, pivot pin 48 for movable handle 40 is inserted into the pivot aperture 23 of the housing component of housing 20 and, thereafter, movable handle 40 is positioned to pivotably couple to housing 20 via pivot pin 48 and such that engagement bulge 51 is operably coupled with mandrel 158 of slider assembly 150, with drive plate 142 and knife plate 172 received within cut-out 49 of movable handle 40. Trigger 72 is then positioned atop and at least partially about movable handle 40, with pivot pin 48 pivotably coupling trigger 72 to housing 20. Biasing spring 71 is also connected for biasing trigger 72 towards the un-actuated position. Linkage 76 is then disposed atop trigger 72 such that peg 77d is pivotably engaged with pivot boss 25 of the housing component of housing 20, coupling tube 78 is received within upper end cam slot 77b of linkage 76, and lower end cam slot 77c of linkage 76 receives post 75c of trigger 72. Thus, trigger and linkage 76 are operably coupled to housing 20, knife plate 172, and one another.

Once the internal components within housing 20 are assembled and in place, as detailed above, the outer housing components of housing 20 are positioned such that the outer housing components cooperate to enclose the internal components. The outer housing components may be engaged with one another in any suitable fashion, e.g., screws, snap-fit engagements, ultrasonic welding, adhesion, etc.

Finally, testing is performed to ensure that surgical instrument 10 is working properly. Such testing may include jaw force testing; testing using a gauge pin (not shown) to test the maximum jaw aperture between jaw members 110, 120 at the distal tips thereof; cut testing of the knife blade 174 using cut test media (not shown); testing of the gap distance between the tissue-contacting surfaces 132a of jaw members 110, 120 (as set by the one or more stop members 132e) in the approximated position thereof at various positions along the lengths of jaw members 110, 120; and/or performing electrical continuity testing.

Figure 31A:
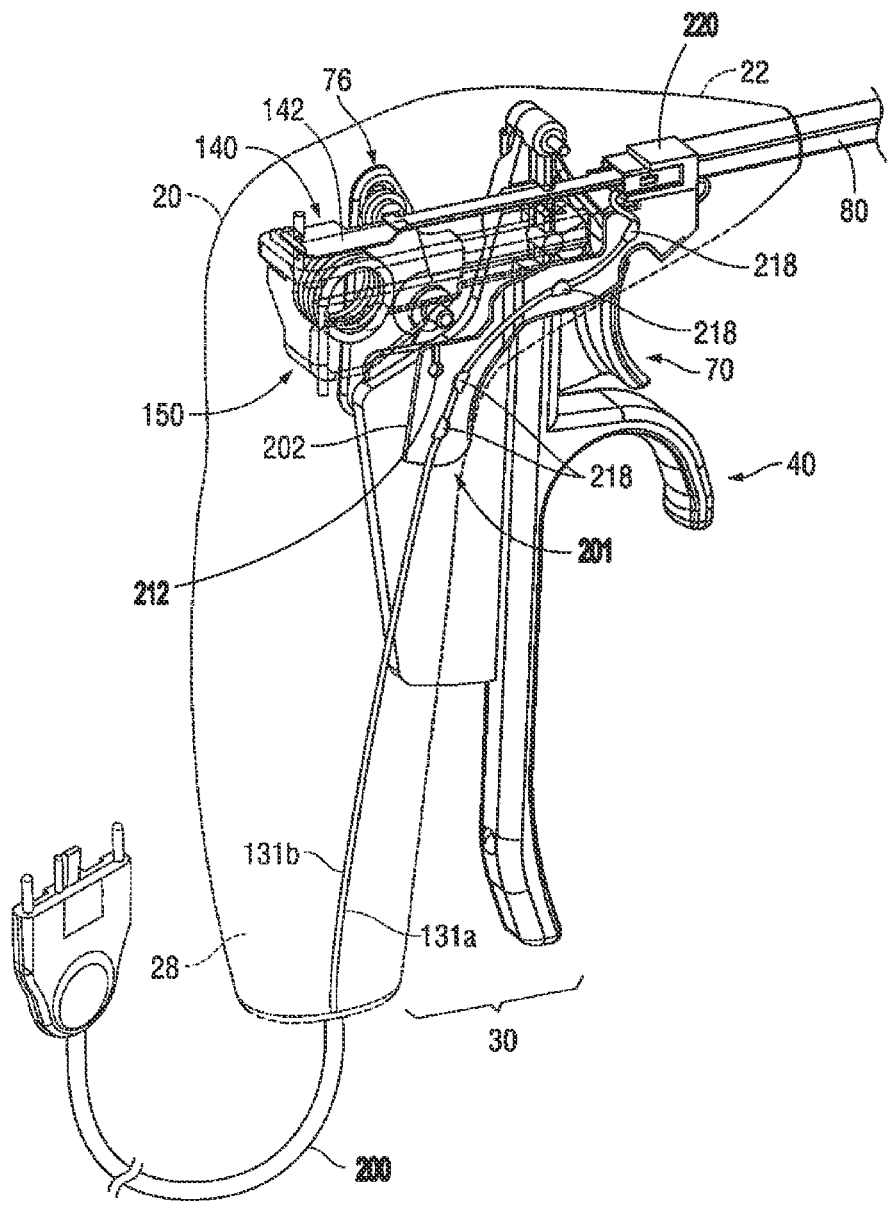
FIG. 31A is a side view of a proximal portion of the surgical instrument of FIG. 1 with components removed to illustrate a wire guide operably coupled to the housing and the shaft of the surgical instrument.
Figure 31B:
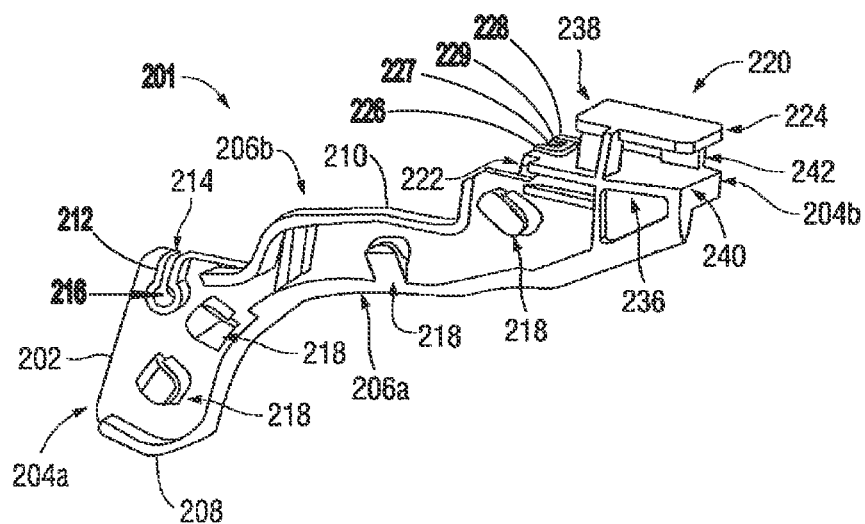
FIG. 31B is a perspective view of the wire guide of FIG. 31A.

FIGS. 31A and 31B show a wire guide 201 that is configured to guide a first electrical wire 131a and a second electrical wire 131b through the housing 20 and into elongated shaft 80 in order to operably couple the generator with energy activation assembly 190 and end effector assembly 100 to enable the selective supply of energy to the end effector assembly 100 via actuation of energy activation assembly 190.

The wire guide 201 includes a body 202, a housing attachment 212, plurality of guiding features 218, and a shaft attachment 220. Body 202 defines a configuration that generally conforms to a portion of housing 20, such as a portion of the inner, concave elbow of the pistol-style configuration of housing 20. The body 202 includes a proximal portion 204a and a distal portion 204b. The proximal portion 204a is aligned with a portion of the fixed handle portion 28 of the housing 20 and the distal portion 204b is aligned with a portion of the barrel portion 22 of the housing 20. The body 202 thus extends from fixed handle portion 28 of housing 20, along the concave elbow of the pistol-style configuration of housing 20, and to the barrel portion 22 of housing 20.

The body 202 further includes a first side 206a and a second side 206b. The first side 206a includes a first spine 208 perpendicularly protruding therefrom. The first spine 208 provides secondary security for the first electrical wire 131a and the second electrical wire 131b. If one or both of the first and second electrical wires 131a, 131b detach from the plurality of guiding features 218 during operation or transportation of instrument 10, the first spine 208 will capture both the first and second electrical wire 131a, 131b and will guide both wires 131a, 131b to the shaft attachment 220. The first side 206a of the body 202 is placed adjacent to the perimeter of the housing 20. In an embodiment, the first side 206a of the body 202 is positioned to rest directly upon the perimeter of the housing 20. In another embodiment, the first side 206a of the body 202 is placed adjacent to the perimeter of housing 20 without contacting the perimeter thereof. The second side 206b of the body 202 includes a second spine 210 that perpendicularly protrudes therefrom. The spine 210 is placed adjacent to other internal components housed within the housing 20 and provides protection to the first electrical wire 131a and the second electrical wire 131b from any potential interference with or damage from the other internal components. The body 202 may be constructed of any appropriate plastic or other suitable material.

The housing attachment 212 is integrally formed within the wire guide 201, although other configurations may alternatively be provided. The housing attachment 212 includes a channel 214 and an aperture 216 both defined therein. Channel 214 and aperture 216 are interconnected in that channel 214 and aperture 216 are in direct communication with one another. Aperture 216 is configured to accept a protrusion 21 (not shown) of the housing 20, which extends from housing 20 inwardly into the cavity defined within housing 20. The wire guide 201 is secured to the housing 20 by the interaction between protrusion and aperture 216 of the housing attachment 212. The protrusion 21 may be positioned within the aperture 216 via sliding through channel 214 or via direct insertion therein. The wire guide 201 remains in a desired position once the protrusion extends through the aperture 216. In another embodiment, the wire guide 201 includes multiple housing attachments 212, which may be integrally formed within the wire guide 201 at designated locations that register with locations of other protrusions of the housing 20 to enable engagement similarly as with protrusion and aperture 216, thus providing multiple attachment points along wire guide 201.

As mentioned above, the wire guide 201 includes a plurality of guiding features 218. In embodiments, each guiding feature 218 of the plurality of guiding features 218 takes the form of a square-shaped hook (FIG. 31B). In such embodiments, the hook portion of each guiding feature 218 extends from the body 202 defining an area therebetween for receipt of the wire(s) 131a, 131b. In another embodiment, each guiding feature 218 of the plurality of guiding features takes the form of a C-shaped hook (not shown). In this embodiment, the hook portion of each guiding feature 218 extends from the body 202 to similarly define an area for receipt of the wire(s) 131a, 131b. In yet another embodiment, each guiding feature 218 of the plurality of guiding features 218 takes the form of a double U-shaped snap lock (not shown). In this embodiment, each double U-shaped snap lock includes three spaced-apart protrusions that extend perpendicular from the body 202. Two spaces between the three spaced-apart protrusions are each configured to secure one of the first and second electrical wires 131a, 131b in a serpentine fashion. Each guiding feature 218 is positioned in relation to one another to allow an appropriate amount of space between each guiding feature 218 while providing support for the first and second electrical wire 131a, 131b.

In embodiments, each guiding feature 218 is integrally formed with the wire guide 201. Additionally, in embodiments, each guiding feature 218 is configured to secure both the first and second electrical wires 131a and 131b to designated locations corresponding to the positions of guiding features 218 on the wire guide 201 such that the plurality of guiding features 218 provide guidance for both the first and second electrical wires 131a, 131b from the fixed handle portion 28 of housing 20, through the barrel portion 22 of housing 20, to the shaft attachment 220, as detailed further below.

Shaft attachment 220 includes a proximal end portion 222, a distal end portion 224, a first wire snap feature 226, a second wire snap feature 228, and a shaft passageway 236. The first wire snap feature 226 and the second wire snap feature 228 are defined in the proximal end portion 222 of the shaft attachment 220 and each includes a channel 227, 229, respectively. Each channel 227, 229 is defined in the proximal end portion 222 of the shaft attachment 220.

Further, channel 227 is generally parallel to channel 229 with a finger separating them. Both channels 227 and 229 are similarly configured, with channel 227 configured to secure the first electrical wire 131a to the shaft attachment 220 while channel 229 is configured to secure the second electrical wire 131b to the shaft attachment 220. The first and second wire snap features 226, 228 both separate and guide the first and second electrical wire 131a, 131b into shaft 80 and to the electrically-conductive plate 132 of each jaw member 110, 120 for electrical connection therewith. Wires 131a, 131b are inserted through wire snap features 226, 228, respectively, flexing snap features 226, 228 to permit passage of wires 131a, 131b into channels 227, 229, respectively. Once wires 131a, 131b are positioned within channels 227, 229, respectively, snap features 226, 228 are returned to their at-rest positions securing wires 131a, 131b within channels 227, 229, respectively, and inhibiting backing-out of wires 131a, 131b.

Referring generally to FIGS. 1-10, various methods of disassembling the surgical instrument 10 and/or for reprocessing the surgical instrument 10 are disclosed and detailed below. In embodiments, the method includes accessing an interior of the housing 20 of the surgical instrument 10 to expose the slider assembly 150, the elongated outer shaft 80 including the drive plate 142 and the knife assembly 170 extending therethrough, and the torsion spring 160. The method further includes grasping the upper leg 162 of the torsion spring 160 to disengage the upper leg 162 from the slot 144 defined within the drive plate 142, disengaging the drive plate 142 from the slider assembly 150, and removing the torsion spring 160 from the slider assembly 150. In embodiments, the torsion spring 160 is disengaged from the slot 144 defined in the drive plate 142 by rotating the torsion spring 160 in a first direction.

In embodiments, the method may further include removing the pivot pin 103 from the end effector assembly 100 of the surgical instrument 10, exposing the cam pin 105 of the end effector assembly 100, removing the cam pin 105 from the end effector assembly 100, and releasing the end effector assembly 100 from the drive plate 142. In other embodiments, the method may include retaining the elongated outer shaft 80 in place while removing the drive plate 142 and the knife blade 174 of the knife assembly 170 from the elongated outer shaft 80. Still other embodiments may include disengaging the knife blade 174 from the drive plate 142, removing the pair of jaw wires 131a, 131b from the wire guide 201 (see FIGS. 31A and 31B) disposed in the housing 20 by unrouting the wires 131a, 131b therefrom, and/or removing the end effector assembly 100 and the jaw wires 131a, 131b from the distal end 83 of the elongated outer shaft 80.

In yet other embodiments the method may include sterilizing the slider assembly 150, elongated outer shaft 80, end effector assembly 100, wire guide 201 jaw wires 131a, 131b (see FIGS. 31A and 31B), knife assembly 170, knife blade 174, torsion spring 160, and/or drive plate 142.

In embodiments, a method of disassembling the surgical instrument 10 for reprocessing including separating a first housing half 20a of the housing 20 from a second housing half 20b of the housing 20 to expose a front end assembly 350 (See FIG. 6), the trigger assembly 70, and the movable handle 40 of the surgical instrument 10. The front end assembly 350 may include, for example, the elongated shaft 80, the end effector assembly 100, the drive plate 142, and the knife plate 172 of the surgical instrument 10. The method may further includes disengaging the biasing spring 71 from the second housing half 20b to enable removal of the trigger assembly 70 from the surgical instrument 10, removing the pivot pin 48 to enable removal of the movable handle 40 from the second housing half 20b, removing the front end assembly 350 from the second housing half 20b, and sterilizing the front end assembly 350 by autoclaving the front end assembly 350, introducing the front end assembly 350 into a sterilization bath (not shown) and/or applying a pressurized fluid (not shown) to the front end assembly 350.

According to embodiments, a method of disassembling the surgical instrument 10 for reprocessing includes separating the first housing half 20a from the second housing half 20b to expose the front end assembly 350, the trigger assembly 70, and the movable handle 40 of the surgical instrument 10. The method also includes disengaging the biasing spring 71 from the second housing half 20b to enable removal of the trigger assembly 70 from the surgical instrument 10, removing the pivot pin 48 to enable removal of the movable handle 40 from the second housing half 20b, removing the front end assembly 350 from the second housing half 20b, orienting the front end assembly 350 to expose the slider assembly 150, the elongated outer shaft 80 including the drive plate 142 the knife assembly 170 extending therethrough, and the torsion spring 160, grasping the upper leg 162 of the torsion spring 160 to disengage the upper leg 162 from the slot 144 defined within the drive plate 142, disengaging the drive plate 142 from the slider assembly 150, and removing the torsion spring 160 from the slider assembly 150.

In embodiments, the torsion spring 160 is disengaged from the slot 144 defined in the drive plate 142 by rotating the torsion spring 160 in a first direction. In other embodiments, the method may further include removing the pivot pin 103 from the end effector assembly 100 of the surgical instrument 10, exposing the cam pin 105 of the end effector assembly 100, removing the cam pin 105 from the end effector assembly 100, and releasing the end effector assembly 100 from the drive plate 142. In other embodiments the method may include retaining the elongated outer shaft 80 in place while removing the drive plate 142 and the knife blade 174 of the knife assembly 170 from the elongated outer shaft 80. Still other embodiments may include disengaging the knife blade 174 from the drive plate 142, removing the pair of jaw wires 131a, 131b from the wire guide 201 (see FIGS. 31A and 31B) disposed in the housing 20 by unrouting the wires 131a, 131b therefrom, and/or removing the end effector assembly 100 and the jaw wires 131a, 131b from the distal end 83 of the elongated outer shaft 80.

In still other embodiments, the method may include sterilizing the slider assembly 150, elongated outer shaft 80, end effector assembly 100, wire guide 201 jaw wires 131a, 131b (see FIGS. 31A and 31B), knife assembly 170, knife blade 174, torsion spring 160, and/or drive plate 142.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of disassembling a surgical instrument for reprocessing, the method comprising:
   separating a first housing half of a housing from a second housing half of the housing to expose a front end assembly, a trigger assembly, and a movable handle of a surgical instrument, the housing having a distal end portion;
   disengaging a biasing spring from the second housing half to enable removal of the trigger assembly from the surgical instrument;
   removing a pivot pin to enable removal of the movable handle from the second housing half;
   disengaging a torsion spring from a drive plate of the front end assembly by moving a portion of the torsion spring toward the distal end portion of the housing to rotate the torsion spring;

removing the front end assembly from the second housing half; and sterilizing the front end assembly.

2. The method according to claim 1, wherein sterilizing the front end assembly includes at least one of autoclaving the front end assembly, introducing the front end assembly into a sterilization bath, or applying a pressurized fluid to the front end assembly.

3. The method according to claim 1, further comprising orienting the front end assembly to expose a slider assembly, the torsion spring, and an elongated outer shaft including a drive plate.

4. The method according to claim 3, further comprising disengaging the drive plate from the slider assembly.

5. The method according to claim 3, further comprising disengaging an upper leg of the torsion spring from the drive plate by moving a lower leg of the torsion spring toward a distal end portion of at least one of the first housing half or the second housing half.

6. The method according to claim 5, further comprising removing the torsion spring from the slider assembly.

7. A method of disassembling a surgical instrument for reprocessing, the method comprising:

exposing, from within a housing of a surgical instrument, a front end assembly, a trigger assembly, and a movable handle, the housing having a distal end portion;

disengaging a biasing spring from the housing to enable removal of the trigger assembly from the surgical instrument;

removing a pivot pin to enable removal of the movable handle from the housing;

disengaging a torsion spring from a drive plate of the front end assembly by moving a portion of the torsion spring toward the distal end portion of the housing to rotate the torsion spring;

removing the front end assembly from the housing; and sterilizing the front end assembly.

8. The method according to claim 7, wherein sterilizing the front end assembly includes autoclaving the front end assembly.

9. The method according to claim 7, wherein sterilizing the front end assembly includes introducing the front end assembly into a sterilization bath.

10. The method according to claim 7, wherein sterilizing the front end assembly includes applying a pressurized fluid to the front end assembly.

11. The method according to claim 7, further comprising orienting the front end assembly to expose a slider assembly, the torsion spring, and an elongated outer shaft including the drive plate.

12. The method according to claim 11, further comprising disengaging the drive plate from the slider assembly.

13. The method according to claim 11, further comprising sterilizing at least one of the slider assembly, the elongated outer shaft, the torsion spring, or the drive plate.

14. The method according to claim 11, wherein disengaging the torsion spring further comprises disengaging an upper leg of the torsion spring from the drive plate by moving a lower leg of the torsion spring toward the distal end portion of the housing.

15. The method according to claim 14, further comprising removing the torsion spring from the slider assembly.

* * * * *